US011272871B2

(12) United States Patent
Block et al.

(10) Patent No.: US 11,272,871 B2
(45) Date of Patent: Mar. 15, 2022

(54) SYSTEM AND METHODS FOR IMPROVING DIAGNOSTIC EVOKED POTENTIAL STUDIES FOR FUNCTIONAL ASSESSMENTS OF NERVES AND NERVE PATHWAYS

(71) Applicant: SidewayStrategies LLC, Walnut Creek, CA (US)

(72) Inventors: Jonathan D. Block, Walnut Creek, CA (US); Hieu T. Ball, Walnut Creek, CA (US)

(73) Assignee: SidewayStrategies LLC, Walnut Creek, CA (US)

( * ) Notice: Subject to any disclaimer, the term of this patent is extended or adjusted under 35 U.S.C. 154(b) by 535 days.

(21) Appl. No.: 16/317,221

(22) PCT Filed: Jul. 14, 2017

(86) PCT No.: PCT/US2017/042271
§ 371 (c)(1),
(2) Date: Jan. 11, 2019

(87) PCT Pub. No.: WO2018/014007
PCT Pub. Date: Jan. 18, 2018

(65) Prior Publication Data
US 2019/0239763 A1 Aug. 8, 2019

Related U.S. Application Data

(60) Provisional application No. 62/362,523, filed on Jul. 14, 2016.

(51) Int. Cl.
*A61B 5/24* (2021.01)
*A61B 5/00* (2006.01)
(Continued)

(52) U.S. Cl.
CPC ............... *A61B 5/24* (2021.01); *A61B 5/377* (2021.01); *A61B 5/4047* (2013.01);
(Continued)

(58) Field of Classification Search
CPC ......... A61B 5/24; A61B 5/377; A61B 5/4047; A61B 5/6814; A61B 5/6828;
(Continued)

(56) References Cited

U.S. PATENT DOCUMENTS 7,231,256 B2   6/2007   Wahlstrand et al.
7,522,953 B2   4/2009   Kaula et al.
(Continued)

FOREIGN PATENT DOCUMENTS

EP      2289448         3/2011
WO      WO 2014/063163  4/2014
WO      WO 2018/014007  1/2018

OTHER PUBLICATIONS

Bernard et al., "Electrical Performances of a New Multipolar Micro-Stimulator"; 10th Annual Conference of the International FES Society, Montreal Canada, Jul. 2005; 3 pages.
(Continued)

*Primary Examiner* — Patrick Fernandes
(74) *Attorney, Agent, or Firm* — Knobbe Martens Olson & Bear LLP

(57) ABSTRACT

Systems and methods for enhancing diagnostic evoked potential recordings of a nerve or nerve pathway of interest. A grid array of stimulating electrodes are placed on, over, or through skin in a location beneath which a nerve or nerve pathway is suspected to lie. A stimulator controls the grid array, where each electrode is independently controllable as active or inactive, as a cathode or anode, etc. A plurality of recording electrodes may record Somato-Sensory Evoked Potentials (SSEPs) and/or Transcranial Electrical Motor
(Continued)

Evoked Potentials (TCeMEP) in response to activation of the stimulating electrodes. A processor controls stimulating the stimulating electrodes, and receives responses from the recording electrodes, in a general search mode and a focused search mode in order to use a minimum stimulation intensity at which a maximum response amplitude is detected to continually stimulate the nerve or the nerve pathway.

20 Claims, 12 Drawing Sheets

(51) Int. Cl.
 *A61N 1/36* (2006.01)
 *A61B 5/377* (2021.01)
 *A61N 1/04* (2006.01)
 *A61N 1/05* (2006.01)

(52) U.S. Cl.
 CPC .......... *A61B 5/6814* (2013.01); *A61B 5/6828* (2013.01); *A61B 5/6829* (2013.01); *A61N 1/36017* (2013.01); A61B 5/4052 (2013.01); A61B 2562/0209 (2013.01); A61B 2562/046 (2013.01); A61N 1/0456 (2013.01); A61N 1/0476 (2013.01); A61N 1/0502 (2013.01)

(58) Field of Classification Search
 CPC ................ A61B 5/6829; A61B 5/4052; A61B 2562/0209; A61B 2562/046; A61B 1/36146; A61B 5/4893; A61B 55/389; A61B 5/4041; A61B 5/407; A61N 1/36017; A61N 1/36125; A61N 1/0456; A61N 1/0476; A61N 1/0502; A61N 1/0051; A61N 1/36071; A61N 1/36021
 See application file for complete search history.

(56) References Cited

U.S. PATENT DOCUMENTS

| | | | |
|---|---|---|---|
| 7,959,577 | B2 | 6/2011 | Schmitz et al. |
| 7,962,191 | B2 | 6/2011 | Marino et al. |
| 8,005,535 | B2 | 8/2011 | Gharib et al. |
| 8,137,284 | B2 | 3/2012 | Miles et al. |
| 8,165,653 | B2 | 4/2012 | Marino et al. |
| 8,172,750 | B2 | 5/2012 | Miles et al. |
| 8,206,312 | B2 | 6/2012 | Farquhar |
| 8,224,453 | B2 | 7/2012 | De Ridder |
| 8,644,903 | B1 | 2/2014 | Osa et al. |
| 8,660,657 | B2 | 2/2014 | Saoji |
| 8,914,121 | B2 | 12/2014 | Moffitt et al. |
| 8,942,801 | B2 | 1/2015 | Miles et al. |
| 9,248,279 | B2 | 2/2016 | Chen et al. |
| 10,016,142 | B2 | 7/2018 | Block et al. |
| 10,973,451 | B2 | 4/2021 | Block et al. |
| 2005/0182456 | A1 | 8/2005 | Ziobro et al. |
| 2006/0161235 | A1 | 7/2006 | King |
| 2006/0276853 | A1 | 12/2006 | Tass et al. |
| 2008/0167574 | A1 | 7/2008 | Farquhar |
| 2009/0177112 | A1 | 7/2009 | Gharib et al. |
| 2010/0268298 | A1 | 10/2010 | Moffitt et al. |
| 2011/0082383 | A1 | 4/2011 | Cory et al. |
| 2011/0230785 | A1 | 9/2011 | Higgins et al. |
| 2011/0269172 | A1 | 11/2011 | Eberle et al. |
| 2012/0095360 | A1 | 4/2012 | Runney et al. |
| 2013/0035741 | A1 | 2/2013 | Kolen et al. |
| 2013/0131743 | A1 | 5/2013 | Yamasaki et al. |
| 2014/0057232 | A1 | 2/2014 | Wetmore et al. |
| 2014/0378941 | A1 | 12/2014 | Su et al. |
| 2015/0005680 | A1 | 1/2015 | Lipani |
| 2015/0012067 | A1 | 1/2015 | Bradley et al. |
| 2015/0012068 | A1 | 1/2015 | Bradley et al. |
| 2015/0032022 | A1 | 1/2015 | Stone et al. |
| 2015/0057722 | A1 | 2/2015 | Faltys et al. |
| 2015/0066104 | A1 | 3/2015 | Wingeler et al. |
| 2015/0157626 | A1 | 6/2015 | Cohen et al. |
| 2016/0022992 | A1 | 1/2016 | Franke et al. |

OTHER PUBLICATIONS

International Search Report in PCT/US2013/065968, dated Jan. 30, 2014, in 2 pages.
Written Opinion of the International Searching Authority in PCT/US2013/065968, dated Jan. 30, 2014, in 10 pages.
Ahmadian A et al., "Analysis of lumbar plexopathies and nerve injury after lateral retroperitoneal transpsoas approach: Diagnostic standardization," J Neurosurg Spine 2013; 18(3); pp. 289-297.
Silverstein J et al., "Saphenous nerve somatosensory evoked potentials: A novel technique to monitor the femoral nerve during transpsoas lateral lumbar interbody fusion," Spine (Phila Pa 1976) 2014; 39(15); pp. 1254-1260.
Robinson LR et al., "The efficacy of femoral nerve intraoperative somatosensory evoked potentials during surgical treatment of thoracolumbar fractures," Spine (Phila Pa 1976) Oct. 1, 1993; 18(13); pp. 1793-1797.
Block J et al., "Motor evoked potentials for femoral nerve protection in transpsoas lateral access surgery of the spine," Neurodiagnostic Journal, Mar. 2015; 55(1); pp. 36-45.
Chaudhary K et al., "Trans-cranial motor evoked potential detection of femoral nerve injury in transpsoas lateral lumbar interbody fusion," Journal of Clinical Monitoring and Computing, Jun. 17, 2015, pp. 549-554.
International Search Report and Written Opinion of the International Searching Authority in PCT/US2017/042271, dated Sep. 26, 2017, in 16 pages.
International Search Report and Written Opinion of the International Searching Authority in PCT/US2017/041995, dated Sep. 28, 2017, in 8 pages.

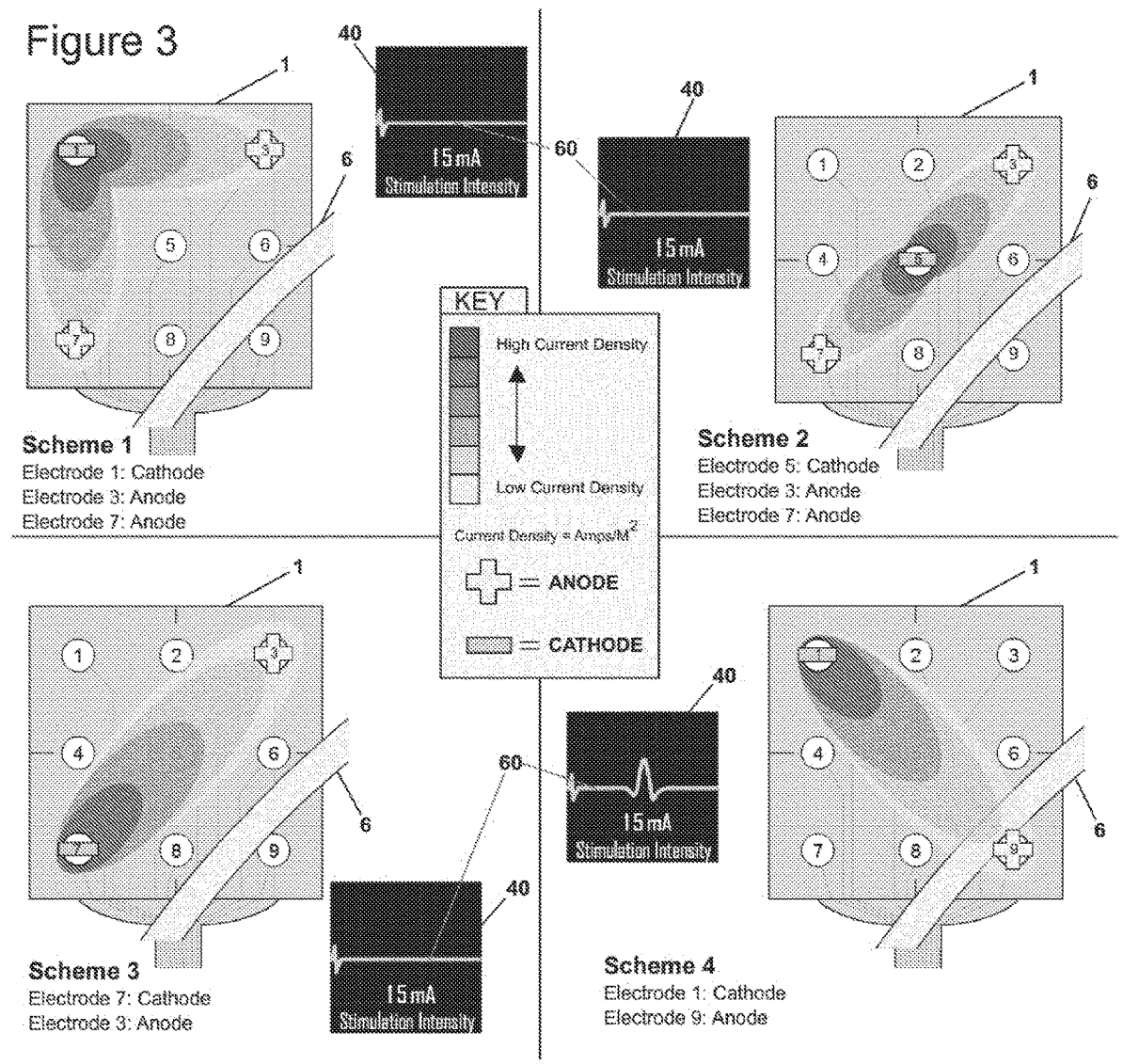

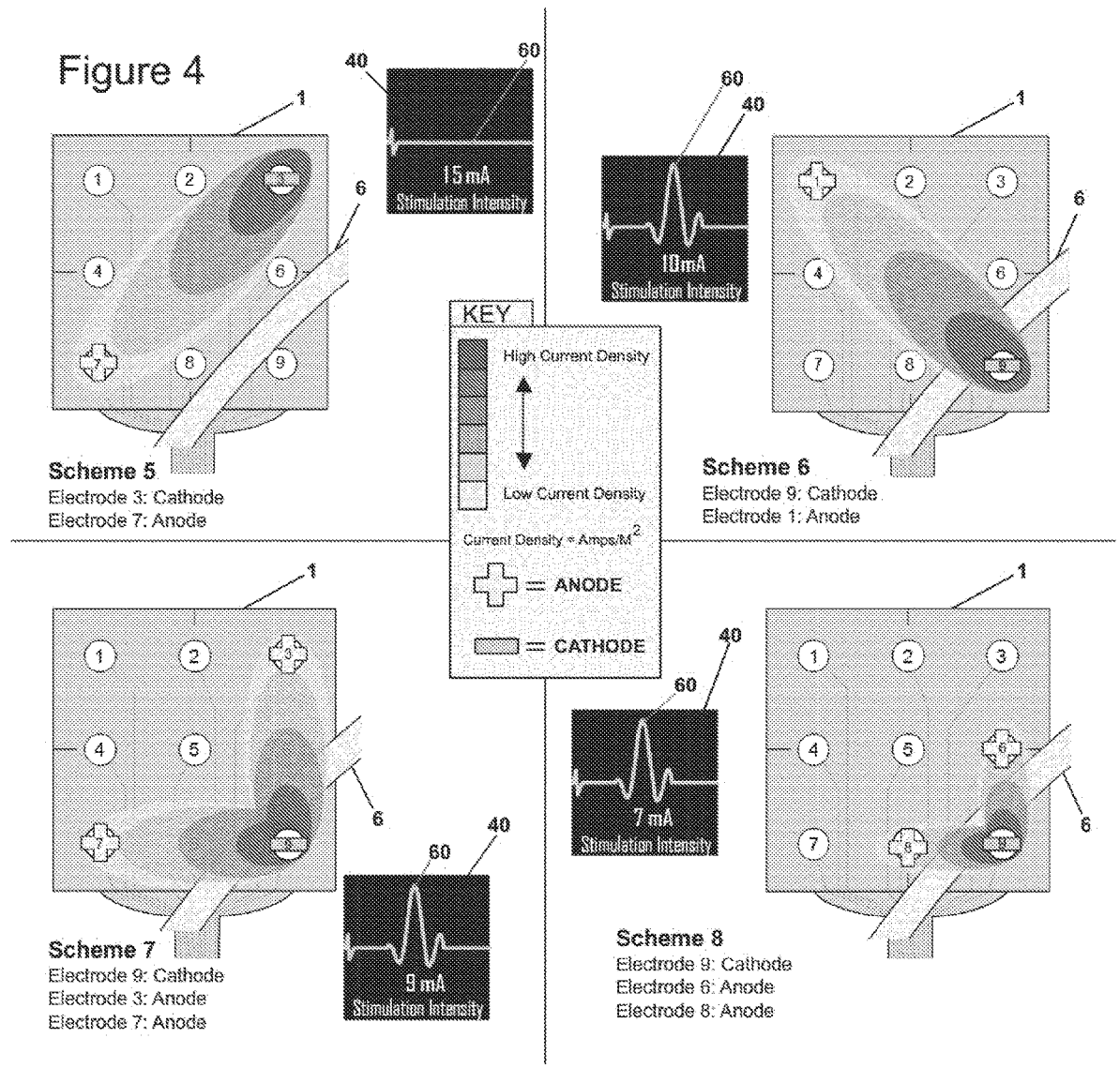

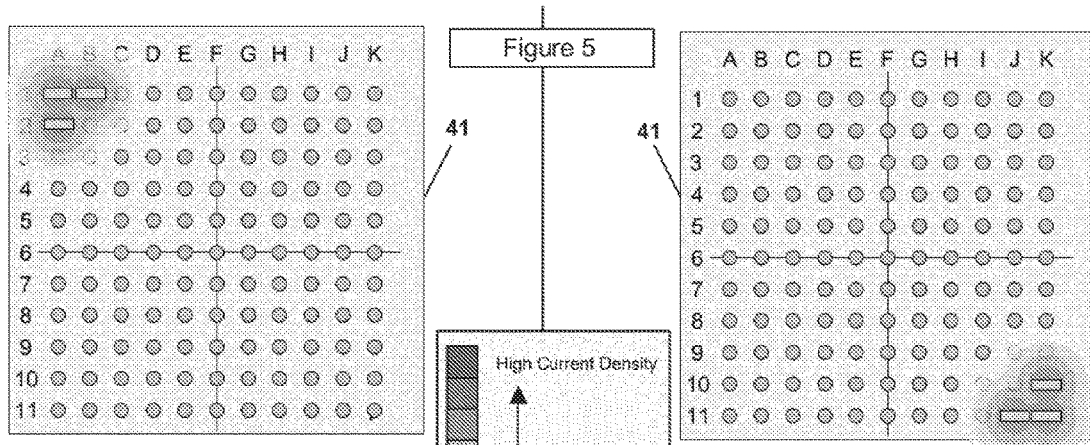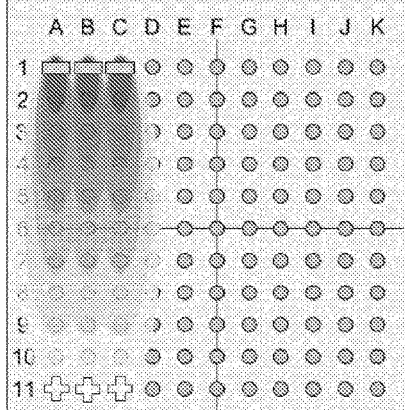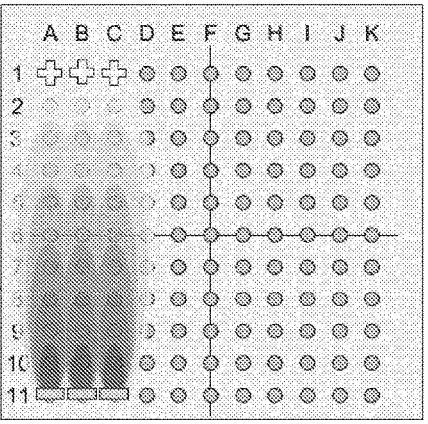

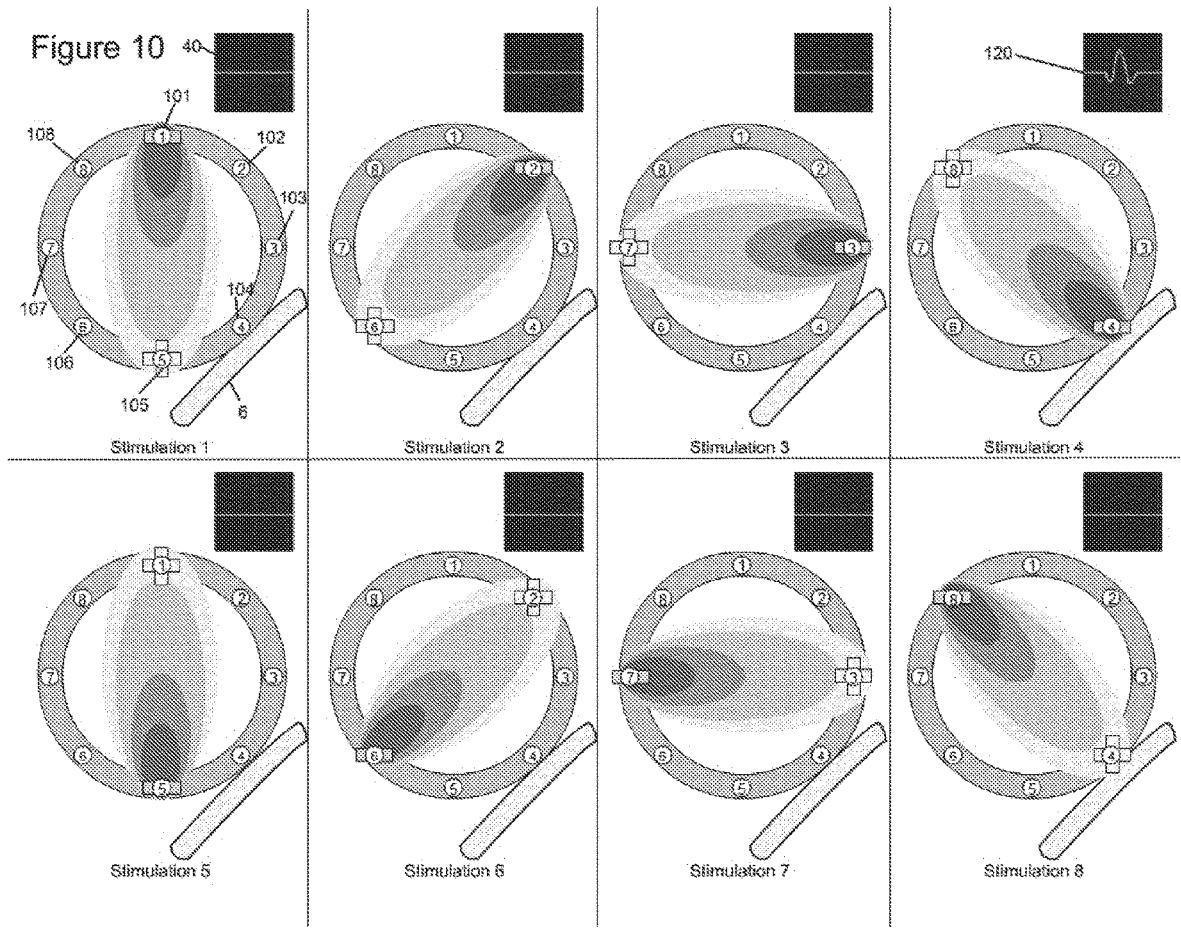
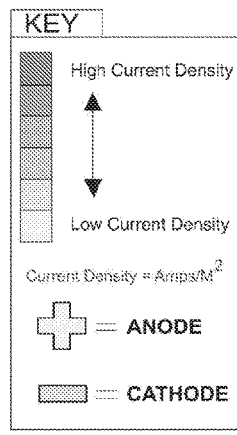

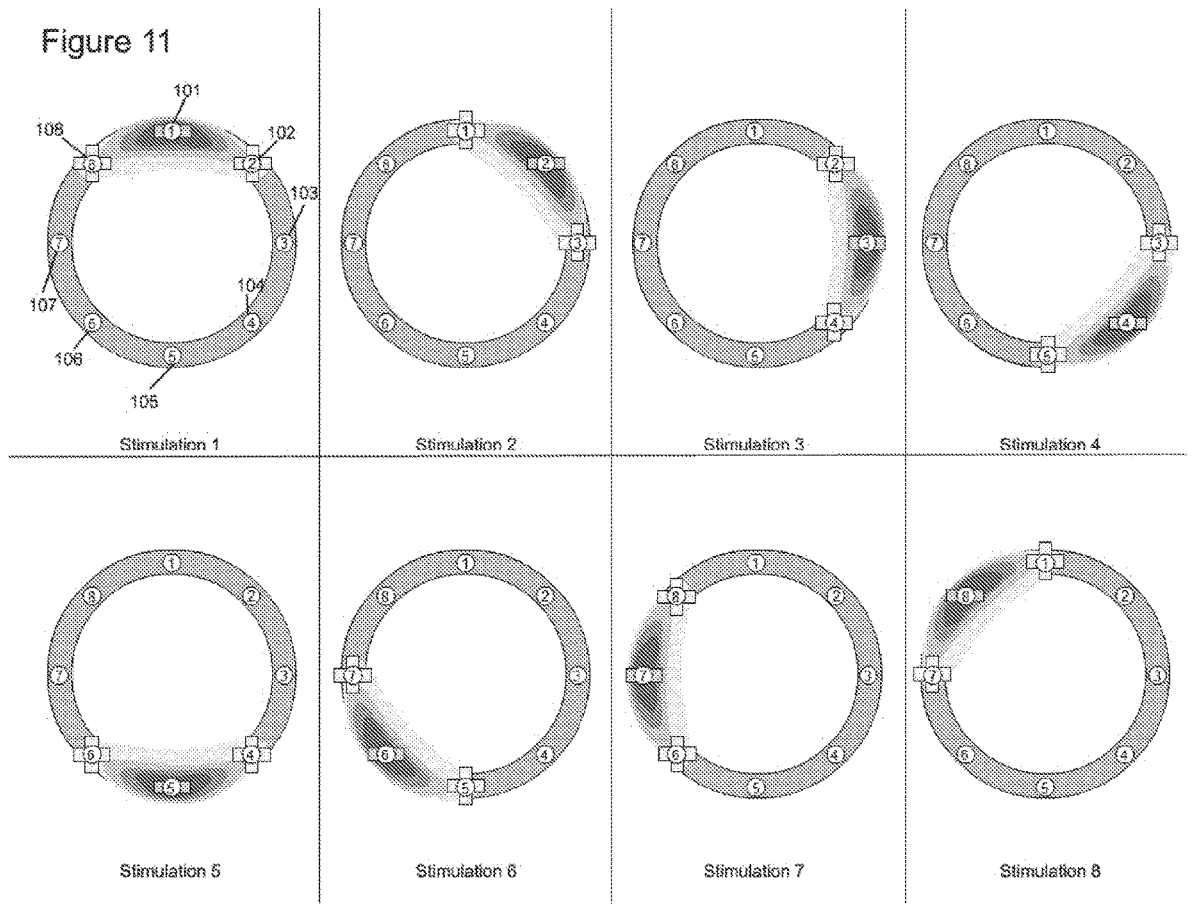
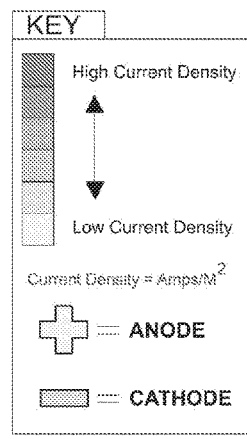
Figure 11

SYSTEM AND METHODS FOR IMPROVING DIAGNOSTIC EVOKED POTENTIAL STUDIES FOR FUNCTIONAL ASSESSMENTS OF NERVES AND NERVE PATHWAYS

INCORPORATION BY REFERENCE OF ANY PRIORITY APPLICATIONS

This application claims priority benefit of U.S. Provisional Patent Application No. 62/362,523, filed Jul. 14, 2016, which is incorporated herein by reference in its entirety for all purposes. Any and all applications related thereto by way of priority thereto or therefrom are hereby incorporated by reference in their entirety.

BACKGROUND

Evoked potentials are commonly utilized in a variety of clinical and surgical applications to provide a functional assessment of neurological structures and pathways. Evoked potentials are obtained by utilizing electrical stimulating electrodes to activate nerves or nerve pathways while simultaneously recording the resultant neural activity and/or muscle responses at a distance from the site of electrical stimulation. In common practice. Evoked potential recordings using traditional stimulation and recording techniques can often be sub-optimal, with poor quality or even unobtainable responses due to variable neuroanatomy, sub-optimal placement of the stimulating electrodes and/or sub-optimal choices of electrical stimulation parameters.

The materials and methods herein describe a novel way to optimize evoked potentials with the goal of providing more useful neurological functional assessments with a higher quality and greater consistency compared to existing commonly utilized techniques. These materials and methods are designed to overcome a host of technical factors that often lead to sub-optimal evoked potential responses that yield less clinical utility. These materials and methods are designed to significantly improve the quality and utility of evoked potential recordings in both clinical and intraoperative settings and reduce uncertainty regarding the accuracy of evoked potential studies.

These materials and methods are designed to reduce common types of user error and provide higher quality evoked potential recordings using specialized hardware that may include various embodiments of stimulating electrode grid arrays which are integrated with specialized software designed to mathematically determine the optimal choice of active stimulating electrodes and the optimal choice of stimulation parameters which yield the highest quality of evoked potential responses.

Stimulating using grid electrode arrays have been used in multiple applications including functional electrical stimulation, cochlear implants, spinal cord stimulators, direct cortical stimulation and deep brain electrical stimulation techniques. Grid electrode designs have been proposed for applications such as functional electro-stimulation using a matrix of surface grid electrodes to apply transcutaneous electrical stimulation for the purpose of pain relief. Microelectrode grid arrays have been proposed for holding tissue slices for recording and/or stimulating neuron cells within the tissue slice. Grid electrode systems have been utilized for recording of electroencephalography (EEG) for recording and stimulation of the cerebral cortex. Grid stimulation techniques have been utilized in intraoperative direct brain stimulation where a grid system of electrodes is utilized for stimulation of the cerebral cortex combined with electromyographic feedback for the purpose of mapping the cortical surface. Other uses of grid electrodes includes implanted grid electrodes that have been utilized with spinal cord stimulators for the purpose of pain control. These systems utilize multiple electrodes on a grid electrode are surgically implanted in proximity to the spinal cord for the purpose of pain control. Spinal cord stimulators utilize different configurations of active electrodes and stimulation parameters for the purpose of selectively stimulating sensory neural pathways until the clinical goal of a subjective reduction in pain in achieved. Similar concepts utilizing multiple electrodes to stimulate neural tissue can also be found in other applications such as deep brain stimulation where implanted electrode arrays are activated with different combinations of active electrodes and stimulation parameters to selectively effect neurological structures deep in the brain for the treatment of movement disorders as well as other brain disorders. Other patent applications have been filed describing automated systems for the acquisition of sensory evoked potential recordings.

None of these examples of utilize the unique materials and methods to optimize evoked potential recordings for intraoperative or clinical functional assessments of nerves or nerve pathways. Similar methods of multi-polar electrical stimulation have been proposed in a previously submitted patent application by the same authors, for example as disclosed in U.S. Patent Pub. No. 2014/0114168, which is hereby made part of this specification as if set forth fully herein and incorporated by reference for all purposes, for all that it contains.

To our knowledge, the specific application of multi-polar stimulation using a grid electrode system has not been proposed for optimizing nerve evoked potential recordings. These materials and methods described herein may be highly beneficial in a variety of clinical and intraoperative settings when a functional assessment of neurological structures and pathways may be desired. These materials and methods are designed to overcome a host of technical difficulties that often reduce the accuracy, quality and utility of evoked potential recordings using traditional nerve stimulation methods.

SUMMARY

The materials and methods described herein describe a novel way to improve the quality, consistency and overall utility of evoked potential recordings by optimizing the electrical activation of nerves or nerve pathways. Traditionally, electrical stimulation of nerves or nerve pathways for clinical and intraoperative evoked potential recordings are usually accomplished with a single pair of electrodes utilizing either a bipolar stimulation montage (e.g., a single anode and a single cathode) or a monopolar stimulation montage (e.g., a cathode with a distant anode). The proposed materials and methods of electrical stimulation contained herein differ from the traditional methods of evoked potential stimulation as they consist of a "multi-polar" grid array with multiple electrodes for more precise control the dispersion of electrical current distribution to biological tissue which is used with brief bursts of stimulation using multiple permutations of active electrode configurations to determine the optimal activation of nerves. One of the main goals of the system is to determine the optimal combination of "active" electrodes on the grid and the optimal stimulation parameters that utilize the least amount of electrical stimulation current to obtain optimal evoked potential recordings. The grid array is powered by a multi-channel electrical power source which is controlled by a software/hardware system that is designed to precisely deliver brief pulses of electrical current to any combination of active electrodes on the grid while simultaneously recording for evoked responses with a differential amplification system. This stimulation system is considered to be "multi-polar" and for each brief pulse of stimulation to the grid, each independent electrode on the grid can be designated with a polarity as an anode, a cathode or rendered electrically inactive. Different patterns of active electrodes on the grid or "schemes" will create different spatial distributions of electrical current densities surrounding the grid, each of which may or may not elicit an evoked response depending on if the particular pattern and parameters of stimulation delivers sufficient current to activate a nearby neural tissue and evoke a recordable evoked response. Each individual pulse of stimulation to the grid is associated with a brief period of recording using a differential electrical amplification system to detect any evoked potential responses. The analog differential amplifier recordings can be digitized and specialized software will provide a rapid mathematical analysis of any evoked potential waveforms associated with each particular pattern of stimulation. There may be a manual mode of operation where the stimulation configurations and parameters can be controlled and set manually by an operator who can manually apply different stimulation configurations and parameters for a manual assessment of different combinations of stimulating electrodes on the resultant evoked potential recordings. Most of what is described herein refers to the proposed system's automated modes, where the system can include various programs that can systematically scan through different stimulation configurations and parameters to search for the presence of any evoked potential responses by scanning the grid. If an evoked response is generated by electrical stimulation utilizing a particular stimulation scheme, the system measures multiple metrics of the resultant waveform morphology that might include parameters such as amplitude, latency, area under the curve as well as other quantitative measurements of the evoked potential waveform. In addition, other mathematical measurements of the response's stability and reproducibility over time may be implemented and found to be helpful in determining the optimal stimulation configuration and parameters. The system utilizes algorithms that will analyze the evoked potential responses associated with each particular burst of current associated with each stimulation scheme and stimulation parameters. In an automated search mode, the system will be designed to alter subsequent stimulation schemes to favor schemes that improve the evoked potential responses until the system mathematically determines the most efficient stimulation scheme and stimulation parameters that yield optimal evoked potential responses. Very basic examples of how the mathematical programming of stimulation sequences might be utilized are described herein. The actual mathematical parameters that will define each automated stimulation sequence might be determined by experimental methods, mathematical modeling or altered from experience with a working unit. Regardless, it should be apparent how various methods of mathematical programming could be implemented.

For testing each stimulation scheme, the system will systematically ramp up the stimulation intensity until either a maximum amplitude evoked potential response is obtained or a maximum predetermined first stimulation intensity is reached. This first or maximum stimulation intensity to be utilized can be limited by safety guidelines for electrical stimulation. The maximum stimulation intensity for a particular application will likely be based on a number of contributing factors including the size of the electrodes in the grid, the spacing of the electrodes, the type of stimulation utilized, the stimulation reputation rate and calculations of the total charge delivered. The system will examine multiple stimulation schemes in this manner to determine which of the scheme(s) yields the maximum quality evoked potential while utilizing the least amount of stimulation intensity.

In general, it is expected that the system would employ methods that begin by scanning with schemes that represent general regions of the grid by delivering current to active electrodes which are thought to produce generalized current densities in a particular section of the grid for a more generalized gross scan for any responses on the grid. This initial more generalized scan may be referred to as a "General Search Mode". The general search mode utilizes stimulation schemes thought to be more sensitive rather than specific, covering larger sub-sections of the grid to grossly detect evoked responses in particular regions or areas of the grid. Based on the responses obtained from the general scan mode, the software is designed to alter subsequent electrical output to the grid to systematically hone in on the optimal stimulation parameters by favoring stimulation patterns and parameters that yield higher quality evoked potential responses. Once evoked potentials are detected, the system moves to what can be referred to as "Focused Search Mode" where the system is designed to systematically utilize more specific stimulation schemes to hone in on the optimal stimulation pattern(s) and parameters that yield an optimal evoked potential response while utilizing the least amount of electrical stimulation. Although an "optimal evoked response" is often determined by the maximum response amplitude, the optimal response can be defined by any of multiple metrics relating to the resultant evoked potential response waveform morphology including, for example, area under the curve, latencies, measurements of repeatablility or other any other useful quantifiable measures.

Applications for this these materials and methods contained herein are diverse. Optimization of evoked potentials may prove to be extremely useful in the clinical assessment of the nervous system and assist in the diagnosis of neuromuscular disorders. For example, these materials and methods can be applied to common clinical nerve conduction studies. This can be accomplished using a small hand-held stimulating grid (shown in FIG. 12) or even a disposable, flexible plastic grid placed or applied with adhesive to the patient's skin (not shown). These multi-polar grids could be utilized to optimize evoked sensory, motor or mixed nerve responses as are commonly recorded in nerve conduction studies which will provide significant advantages over traditional means of nerve stimulation that utilize simple bipolar stimulation configurations (1 anode and 1 cathode).

A grid stimulation system could have multiple advantages in clinical nerve conduction studies. It may serve to limit the amount of patient discomfort by rapidly determining the least amount of electrical stimulation intensity to obtain an optimal or useful recorded evoked response. These materials and methods might also make it possible to obtain useful nerve conduction studies from nerves that are often difficult to assess, with the ability to elicit responses that might otherwise be unobtainable with conventional bipolar nerve conduction stimulation techniques. For example, these materials and methods may be useful for providing assessments of diseased nerves which often yield lower amplitude or desynchronized responses that might otherwise be poor in quality or unobtainable using conventional methods of stimulation and recording. These materials and methods might also be useful in obtaining evoked responses from nerves that are commonly difficult to electrically activate due to their variable anatomical courses between patients. For example, these materials and methods might be useful for obtaining a functional assessment of the lateral femoral cutaneous nerve which has a considerably variable anatomical course between different individuals. In clinical nerve conduction studies, responses from the lateral femoral cutaneous nerve are often unobtainable and useful evoked responses are often difficult to obtain even in normal patients.

For nerve conduction testing applications, these systems and methods can be modified to record Compound Muscle Action Potentials (CMAPs), Sensory Nerve Action Potentials (SNAPs) and Mixed Nerve Action Potentials (MNAPs) providing a user with a functional assessment of the peripheral motor, sensory and mixed nerve function. The search modes can enhance the ability to detect the stimulation intensity where the electrical stimulation results in a maximum amplitude CMAP, SNAP or MNAP response where the response does not increase in amplitude with increasing stimulation intensity. The maximum amplitude of the evoked response suggests that all of the axons in the nerve of interest have been maximally activated. These techniques can be a great clinical value that offer an increased confidence that a decreased amplitude of an evoked response is likely caused by pathology and not by technical factors such as inadequate stimulation.

These methods can enhance the operators ability to acquire clinically useful evoked potentials in nerves that are technically challenging to stimulate due to anatomical variability in the position of the nerves from patient to patient or technically challenging for other reasons including but not limited to; the presence of diseased nerves, small caliber nerves, edematous extremities, dry or scaly skin or with patients with a large body habitus.

For nerve conduction study applications, multiple stimulating grid electrodes can be utilized to stimulate at multiple points along the course of the nerve where search modes may be independently applied in order to provide assessments of peripheral nerve function at two or more points of a nerve to provide functional assessments of segments of a nerve. Multiple evoked potential recordings can be utilized from two separate stimulation sites at a known distance apart in order to calculate nerve conduction velocity. These optimized stimulation techniques for nerve conduction studies may also be useful to elicit additional nerve conduction studies including F-responses and H-reflex responses.

For nerve conduction study applications, the search modes can be modified to be utilized in a clinical setting on awake patients where the electrical stimulation is often poorly tolerated or even painful for the patient. The operator of the system can use their judgement to acquire the most useful and clinically relevant information from the examination and try to minimize the discomfort or pain experienced by the patient which may even cause the testing to be aborted. Additional safety and comfort mechanisms may be added to these systems for electrical stimulation for awake patients. The system may include a hand-held safety button that a patient can press to immediately turn off the electrical stimulation if the patient is unable to tolerate the electrical stimulation, which can be intolerable to some patients, especially at higher stimulation intensities.

For nerve conduction testing on awake patients in a clinical setting, the system may include operator controls to alter or modify the fully automated search modes that might be utilized in patients under anesthesia where discomfort from the stimulation is not a problem. For nerve conduction testing in awake patients, the operator can acquire the most clinically useful data while delivering as little electrical stimulation as possible. The operator may choose to limit the total number of stimulations and schemes utilized. The operator can assess each patient's ability to tolerate the examination and make judgements on whether they should utilize manual control of the stimulation schemes and stimulation parameters to deliver individual stimulations or if the patient might be able to tolerate a semi-automated search mode protocol.

The number of stimulations to obtain an adequate assessment of the evoked potential and confirm a maximum amplitude response may be limited by the operator, whereas the number of schemes tested may be limited to as little as two, for example in a situation where both schemes resulted in a similar maximum amplitude of the evoked potential response, especially if the recorded maximum amplitude is within the normal range of the lab's established normative data.

In addition to utility in common nerve conduction studies, these materials and methods may have significant utility in intraoperative monitoring of evoked potentials as is described in the main examples illustrated in this publication. For example, these materials and methods may be particularly useful for obtaining evoked potentials from that have been considered challenging to monitor such as the saphenous nerve as is illustrated in the embodiment in FIG. 1.

Similar methods can be modified and applied to other neuromonitoring modalities such as Transcranial Electrical Motor Evoked Potentials (TceMEP) (not shown in illustrations) for providing a user with a functional assessment of motor nerves or nerve pathways during a procedure in which the nerve or nerve pathway is known to be at risk of damage. In this embodiment, the grid of electrodes comprises scalp electrodes placed at specific locations on the scalp that overly the primary motor cortex in order to evoke responses in the descending corticospinal motor tracts. For example, the grid of electrodes are positioned at or in proximity to scalp positions C1, C2, C3, C4, Cz or Fz as defined by the 10-20 System (American Electroencephalographic Society, 1994b). The TCeMEP monitoring embodiment comprises a least one recording channel of electromyographic recordings from at least one muscle, and may include multiple muscle recording channels from the upper and lower extremities, head and trunk. In this embodiment, the system sequentially evaluates multiple stimulation schemes for their ability to evoke a electromyographic muscle response or M response, searching for the most efficient stimulation scheme that evoked a maximum quality (e.g., amplitude) M response while utilizing the least amount of electrical stimulation intensity. The TCeMEP system is configured to test a plurality of stimulation schemes, with each test stimulation comprising or consisting essentially of a rapid train of electrical stimulus pulses with pulse durations ranging from 25-75 microseconds, with the number of pulses ranging from 3-8 and the inter-pulse intervals ranging from 2-4 milliseconds. Searching for the optimal TCeMEP stimulation scheme(s) may be executed in manual, or a semi-automated mode for safety purposes with the operator visually monitoring patient movement that is often an unwanted side effect of transcranial electrical stimulation.

After the optimal stimulation scheme(s) are determined, this stimulation scheme(s) can be utilized to evoke TCeMEP responses which are monitored over time to provide a continuous near-real time assessment of motor nerves and motor pathways during procedures where the nerve or nerve pathways are thought to be at risk for damage. Different TCeMEP stimulation schemes may provide maximal quality (e.g., maximum amplitude) of the M responses in particular neuromuscular distributions that may be the preferred diagnostic information of interest for a given procedure and therefore the user will be able to choose particular stimulation schemes to optimize the monitoring the nerve or nerve pathway of interest.

These same stimulation techniques for TCeMEPs can also be applied to optimize D-wave and I-wave recordings using epidural electrodes to record descending motor pathway activity, for example, in the surgery for intramedullary spinal cord tumors.

It should be appreciated that these concepts may be applied to a variety of applications that include clinical diagnostic studies as well as intraoperative neuromonitoring applications. The main example of these materials and methods described herein is a particular embodiment of a system designed for the purpose of intraoperative monitoring of femoral nerve function for a surgical procedure where it is known to be at risk; a minimally invasive far lateral retroperitoneal trans-psoas lumbar interbody discectomy and fusion procedures at the L4-L5 disc level. This example was chosen because high grade injuries to the femoral nerve have been reported and these injuries can be severely debilitating. Thus, the ability to protect this nerve during these procedures is extremely valuable. This main example illustrates a system designed to optimize the quality of saphenous Somatosensory Evoked Potentials (sSSEPs) which can provide a relatively continuous intraoperative functional assessment of the femoral nerve via stimulation of its' major sensory branch the saphenous nerve. By continually recording evoked responses from a site past the site of the surgery where the nerve is at risk (FIG. 1 arrow), the function of the neural pathway can be assessed and monitored over time. Therefore, any detrimental effects of the surgery on neural function can be detected so that timely countermeasures can be employed to avoid or attenuate impending nerve damage. A significant degradation in the amplitude of the saphenous sensory evoked potential responses may provide an early warning that surgical dilators or retractors may have directly or indirectly compressed or stretched the femoral nerve components or related vasculature to the point where nerve function is failing. Prolonged compression or ischemia to neural structures from surgical instruments is well established as a major cause of iatrogenic neurological injury. The materials and methods described in the main example provided herein is one particular embodiment specifically designed to monitor femoral nerve function using a grid system to optimize Saphenous sensory evoked potentials during a particular type of minimally invasive spine surgery.

Using conventional methods of stimulation for recording evoked potentials, it is considerably more technically challenging to adequately activate deep nerves with variable anatomical courses such as the saphenous nerve compared to more superficial nerves such as the posterior tibial nerve which is commonly used for intraoperative monitoring of the spinal cord sensory pathways. In practice, saphenous nerve sensory evoked potential responses are often significantly lower in amplitude than posterior tibial nerve responses and there are a host of additional factors that often make it considerably more technically challenging to acquire useful saphenous sensory evoked potential recordings compared to evoked potentials from stimulation of posterior tibial nerve at the ankle. Using traditional methods of evoked potential stimulation and recording, it is not uncommon to acquire low amplitude, poor quality or completely unobtainable saphenous sensory evoked potentials. The main example in this publication illustrates how these materials and methods can be applied to overcome some of the limitations and technical hurdles that are encountered with commonly utilized evoked potential stimulation techniques. The goal of certain embodiments is to improve the overall quality, consistency and utility of evoked potential recordings.

In some embodiments, a system is configured to enhance diagnostic evoked potential recordings of a nerve or nerve pathway of interest. The system comprises a plurality of stimulating electrodes arranged in a grid array configured to be placed on, over, or through skin over an area that the nerve or nerve pathway of interest is suspected to lie beneath. The system comprises a stimulator configured to control the grid array. Each of the plurality of stimulating electrodes is independently assignable to be active or inactive. Each of the active electrodes is independently assignable to be an anode or a cathode. The stimulator is configured to independently assign stimulation parameters to each of the active electrodes. The system comprises a plurality of recording electrodes configured to record at least one of Somato-Sensory Evoked Potentials (SSEPs) and Transcranial Electrical Motor Evoked Potentials (TCeMEP). The system comprises a processor configured to automatically execute a general search mode and a focused search mode after the general search mode. The general search mode comprises instructing the stimulator to systematically test a plurality of stimulation schemes until an evoked potential response is detected by the plurality of recording electrodes having a maximum response amplitude. Each said stimulation scheme of the general search mode includes assigning positions of the active electrodes and polarity of the active electrodes. The general search mode further comprises instructing the stimulator to ramp stimulation intensity of a stimulation during testing each said stimulation scheme until either a maximum stimulation intensity value is reached or the maximum evoked potential response amplitude is detected. The maximum evoked potential response amplitude is an evoked potential recording that does not increase in amplitude upon an increase in stimulation intensity. The stimulation scheme at which the maximum response amplitude is detected comprises a positive stimulation scheme. The focused search mode comprises utilizing information from the positive stimulation scheme to instruct the stimulator to systematically test the plurality of stimulation schemes until an evoked potential recording is detected by the plurality of recording electrodes having the maximum response amplitude and a minimum stimulation intensity. The focused search mode further comprises instructing the stimulator to ramp the stimulation intensity during testing each said stimulation scheme until the maximum response amplitude is detected. The focused search mode further comprises recording the stimulation intensity during testing each said stimulation scheme at which the maximum response amplitude is detected, comparing the stimulation intensities at which the maximum response amplitude was detected, and selecting the minimum stimulation intensity at which the maximum response amplitude was detected. The processor is further configured to use stimulation scheme and the minimum stimulation intensity at which the maximum response amplitude was detected to continually stimulate the nerve or the nerve pathway.

The general search mode may further comprise, after the evoked potential recording is detected, executing another stimulation scheme. The electrodes of the grid array may be spaced substantially evenly. The electrodes of the grid array may be arranged in aligned rows and columns having four corners. The electrodes of the grid array may comprise assigning at least two corner positions to the active electrodes during at least one said stimulation scheme. The electrodes of the grid array may comprise assigning at least three corner positions to the active electrodes during at least one said stimulation scheme. The grid array may comprise two rows and two columns. The grid array may comprise three rows and three columns. The grid array may comprise two rows and four columns. The grid array may comprise three rows and six columns. The grid array may comprise eleven rows and eleven columns. The grid array may comprise between two and fifty rows and between two and fifty columns. The grid array may comprise between 2 and 100 rows and between 2 and 100 columns. The grid array may comprise an odd number of rows and an odd number of columns. The grid array may comprise a first number of rows and a second number of columns. The second number may be at least 2 times greater than the first number. The second number may be at least 3 times greater than the first number. The first number may be at least 2 times greater than the second number. The first number may be at least 3 times greater than the second number. The electrodes of the plurality of electrodes may be percutaneous. The electrodes of the plurality of electrodes may be transcutaneous. The electrodes of the grid array may be arranged in a circular pattern. The circular pattern may comprise a ring and an electrode in the ring. The electrodes of the grid array may comprise assigning at least two ring positions to the active electrodes during at least one said stimulation scheme. The electrodes of the grid array may comprise assigning at least three ring positions to the active electrodes during at least one said stimulation scheme. At least one of the electrodes of the grid array may comprise an atraumatic tip. The atraumatic tip may comprise a spherical shape. The atraumatic tip may comprise a planar shape. The grid array may be configured to be placed on a limb.

The grid array may be configured to be placed on a leg. The grid array may be configured to be placed on a thigh. The grid array may be configured to be placed on a calf. The grid array may be configured to be placed on a foot. The grid array may be configured to be placed on an arm. The grid array may be configured to be placed on an upper arm. The grid array may be configured to be placed on a forearm. The grid array may be configured to be placed on a hand. The grid array may be configured to be placed on a head. The plurality of recording electrodes may be configured to be placed on a head. The plurality of recording electrodes may be configured to be placed on a limb. The plurality of recording electrodes may be configured to be placed on a leg. The plurality of recording electrodes may be configured to be placed on a thigh. The plurality of recording electrodes may be configured to be placed on a calf. The plurality of recording electrodes may be configured to be placed on a foot. The plurality of recording electrodes may be configured to be placed on an arm. The plurality of recording electrodes may be configured to be placed on an upper arm. The plurality of recording electrodes may be configured to be placed on a forearm. The plurality of recording electrodes may be configured to be placed on a hand. The plurality of recording electrodes may be configured to be placed on a finger. The plurality of recording electrodes may be configured to be placed on a muscle. The system of Claim 1, wherein the grid array may be configured to be placed on a first appendage and the plurality of recording electrodes may be configured to be placed on a second appendage different than the first appendage. The grid array may be configured to be placed on a first limb and the plurality of recording electrodes may be configured to be placed on a second appendage different than the first limb. The stimulation parameters may be configured to inhibit at least one of discomfort and pain due to overstimulating with intensities that may be above the stimulation intensity. At least one of the stimulator, the general search mode, and the focused search mode may be configured to enhance a user's ability to acquire clinically useful evoked potentials in a nerve that may be technically challenging to stimulate due to at least one of anatomic positional variability, presence of disease, small caliber, edematous extremities, dry or scaly skin, or large body habitus. The grid array may comprise a plurality of smaller grid arrays each configured to stimulate multiple points along a course of the nerve or nerve pathway. The system may further comprise a safety button capable of being pressed by an awake subject to immediately stop the stimulation. The system may further comprise user controls configured to modify at least one of the general search mode and the focused search mode. The controls may comprise a limit on a total number of said stimulation schemes used. The limit on a total number of said stimulation schemes used may comprise two said stimulation schemes. The limit on a total number of said stimulation schemes used may comprise less than ten said stimulation schemes. The processor may be configured to semi-automatically execute the general search mode and the focused search mode after the general search mode. At least one of the general search mode and the focused search mode may be configured to be interrupted by a user. At least one of the general search mode and the focused search mode may be configured to be interrupted by a user visually monitoring the subject for unwanted side effect of the stimulation. The unwanted side effect of the stimulation may comprise patient movement. At least one of the general search mode and the focused search mode may be configured to be interrupted by a user monitoring maximum amplitudes recorded from a plurality of stimulation schemes that re within a normal range of established normative data.

The plurality of recording electrodes may be configured to record Somato-Sensory Evoked Potentials (SSEPs). The SSEPs may provide a user with a continuous functional assessment of the nerve or nerve pathway during a procedure in which the nerve or nerve pathway may be known to be at risk of damage. The SSEPs may comprise at least one of peripheral nerve SSEP recordings, spinal SSEP recordings, subcortical SSEP recordings, and cortical SSEP recordings. During testing at least one said stimulation scheme, the stimulation may comprise a monophasic rectangular pulse having a duration between 100 µs and 1,000 µs and/or a maximum stimulation intensity between 30 mA and 60 mA. During testing each said stimulation scheme, the stimulation may comprise a monophasic rectangular pulse having a duration between 100 µs and 1,000 µs and/or a maximum stimulation intensity between 30 mA and 60 mA. The stimulation may comprise a repetition rate may be between 3 stimulations per second and 11 stimulations per second. The general search mode may comprise testing at least one of the plurality of stimulation schemes a plurality of times and determining a mean average of any evoked potential recordings for said at least one stimulation scheme. The plurality of times may comprise between about 100 times and about 1,000 times dependent on the signal to noise ratio. The nerve or nerve pathway may be a sensory nerve or sensory nerve pathway. The sensory nerve or sensory nerve pathway may comprise at least one of an ulnar nerve, a median nerve, a radial nerve, a musculocutaneous nerve, an antebrachial cutaneous nerve, a lateral femoral cutaneous nerve, a pudendal nerve, a femoral nerve, a sciatic nerve, a posterior tibial nerve, a peroneal nerve, a saphenous nerve, and a sural nerve. A location of damage risk to the nerve or nerve pathway may be between the grid array and the plurality of recording electrodes.

The plurality of recording electrodes may be configured to record Transcranial Electrical Motor Evoked Potentials (TCeMEP). The TCeMEPs may provide a user with a functional assessment of the nerve or nerve pathway during a procedure in which the nerve or nerve pathway may be known to be at risk of damage. The nerve or nerve pathway may be a motor nerve or motor nerve pathway. The grid array may comprise scalp electrodes configured to be placed at locations overlying a primary motor cortex to evoke responses in descending corticospinal motor tracts. The grid array may be configured to be positioned proximate to scalp positions C1, C2, C3, C4, Cz, or Fz as defined by the 10-20 System of the American Electroencephalographic Society. The system may further comprise a muscle recording channel configured to record an electromyographic reading from at least one muscle. The system may further rcomprise a plurality of multiple muscle recording channels including the muscle recording channel. The plurality of muscle recording channels may be configured to record an electromycraphicn readon from at least one of upper extremities, lower extremities, head, and trunk. At least one of the general search mode and the focused search mode may be configured to sequentially evaluate the plurality of stimulation schemes for their ability to evoke a electromyographic muscle response or M response. During testing at least one said stimulation scheme, the stimulation may comprise a rapid train of electrical stimulus pulses having a pulse duration between 25 µs and 75 µs, a number of pulses between 3 and 8, and/or inter-pulse intervals between 2 ms and 4 ms. During testing each said stimulation scheme, the stimulation may comprise a rapid train of electrical stimulus pulses having a pulse duration between 25 µs and 75 µs, a number of pulses between 3 and 8, and/or inter-pulse intervals between 2 ms and 4 ms. At least one of the general search mode and the focused search mode may be configured to use the stimulation scheme and the minimum stimulation intensity at which the maximum response amplitude was detected in a TCeMEP monitoring mode. The TCeMEP monitoring mode may comprise monitoring TCeMEPs over a duration to provide a continuous near real time assessment of motor nerves and motor pathways. The monitoring mode may allow a user to select use of a selected stimulation scheme yielding a response in a neuromuscular distribution of interest as the stimulation scheme in the monitoring mode. A location of damage risk to the nerve or nerve pathway may be between the grid array and the plurality of recording electrodes.

The plurality of recording electrodes may be configured to record Compound Muscle Action Potentials (CMAPs). The CMAPs may provide a user with a functional assessment of the peripheral motor nerve function. The processor may be configured to detect a stimulation intensity at which the stimulation produces a CMAP amplitude that does not increase with increasing stimulation intensity. The processor may be configured to perform an independent search mode to provide an assessment of peripheral nerve motor function for segments of nerves and to acquire CMAP recordings from at least two separate sites at a known distance apart to calculate nerve conduction velocity. The plurality of recording electrodes may comprise an active electrode on a belly of the muscle of interest, a reference electrode between 2 cm and 10 cm away from the active electrode and on the tendon or a nearby electrically inactive region, and a ground electrode configured to reduce artifact effects of the stimulation. The stimulation intensity may be between 1 mA and 60 mA. The stimulation may have a pulse duration between 0.05 ms and 0.2 ms. A location of damage risk to the nerve or nerve pathway may be between the grid array and the plurality of recording electrodes.

The plurality of recording electrodes may be configured to record Sensory Nerve Action Potentials (SNAPs). The SNAPs may provide a user with a functional assessment of the peripheral sensory nerve function. At least one of the general search mode and the focused search mode may be configured to detect a stimulation intensity at which the stimulation produces a SNAP amplitude that does not increase with increasing stimulation intensity. The plurality of recording electrodes may comprise an active electrode, a reference electrode between 2 cm and 10 cm away from the active electrode, and a ground electrode configured to reduce artifact effects of the stimulation. The processor may be configured to perform an independent search mode to provide an assessment of peripheral nerve motor function for segments of nerves and to acquire SNAP recordings from at least two separate sites at a known distance apart to calculate nerve conduction velocity. The stimulation intensity may be between 1 mA and 60 mA. The stimulation may have a pulse duration between 0.05 ms and 0.2 ms. A location of damage risk to the nerve or nerve pathway may be between the grid array and the plurality of recording electrodes.

The plurality of recording electrodes may be configured to record Mixed Nerve Action Potentials (MNAPs). The MNAPs may provide a user with a functional assessment of the peripheral mixed nerve function. The processor may be configured to detect a stimulation intensity at which the stimulation produces a SNAP amplitude that does not increase with increasing stimulation intensity. The plurality of recording electrodes may comprise an active electrode, a reference electrode between 2 cm and 10 cm away from the active electrode, and a ground electrode configured to reduce artifact effects of the stimulation. The processor may be configured to perform an independent search mode to provide an assessment of peripheral nerve motor function for segments of nerves and to acquire MNAP recordings from at least two separate sites at a known distance apart to calculate nerve conduction velocity. The stimulation intensity may be between 1 mA and 60 mA. The stimulation may have a pulse duration between 0.05 ms and 0.2 ms. A location of damage risk to the nerve or nerve pathway may be between the grid array and the plurality of recording electrodes.

In some embodiments, a system is configured to enhance diagnostic evoked potential recordings of a nerve or nerve pathway of interest. The system comprises a plurality of stimulating electrodes arranged in a grid array configured to be placed on, over, or through skin over an area that the nerve or nerve pathway of interest is suspected to lie beneath. The system comprises a stimulator configured to control the grid array. Each of the plurality of stimulating electrodes is independently assignable to be active or inactive. Each of the active electrodes is independently assignable to be an anode or a cathode. The stimulator is configured to independently assign stimulation parameters to each of the active electrodes. The system comprises a processor configured to automatically execute a general search mode and a focused search mode after the general search mode.

The general search mode comprises instructing the stimulator to systematically test a plurality of stimulation schemes until an evoked potential response is detected by the plurality of recording electrodes having a maximum response amplitude. Each said stimulation scheme of the general search mode includes assigning positions of the active electrodes and polarity of the active electrodes. The general search mode further comprises instructing the stimulator to ramp stimulation intensity of a stimulation during testing each said stimulation scheme until either a maximum stimulation intensity value is reached or the maximum evoked potential response amplitude is detected. The maximum evoked potential response amplitude is an evoked potential recording that does not increase in amplitude upon an increase in stimulation intensity. The stimulation scheme at which the maximum response amplitude is detected comprises a positive stimulation scheme. The focused search mode comprises utilizing information from the positive stimulation scheme to instruct the stimulator to systematically test the plurality of stimulation schemes until an evoked potential recording is detected by the plurality of recording electrodes having the maximum response amplitude and a minimum stimulation intensity. The focused search mode further comprises instructing the stimulator to ramp the stimulation intensity during testing each said stimulation scheme until the maximum response amplitude is detected. The focused search mode further comprises recording the stimulation intensity during testing each said stimulation scheme at which the maximum response amplitude is detected, comparing the stimulation intensities at which the maximum response amplitude was detected, and selecting the minimum stimulation intensity at which the maximum response amplitude was detected. The processor is further configured to use stimulation scheme and the minimum stimulation intensity at which the maximum response amplitude was detected to continually stimulate the nerve or the nerve pathway.

In some embodiments, a system is configured to enhance diagnostic evoked potential recordings of a nerve or nerve pathway of interest. The system comprises a plurality of stimulating electrodes arranged in a grid array configured to be placed on, over, or through skin over an area that the nerve or nerve pathway of interest is suspected to lie beneath. The system comprises a stimulator configured to control the grid array. Each of the plurality of stimulating electrodes is independently assignable to be active or inactive. Each of the active electrodes is independently assignable to be an anode or a cathode. The stimulator is configured to independently assign stimulation parameters to each of the active electrodes. The system comprises a processor configured to automatically execute a general search mode. The general search mode comprises instructing the stimulator to systematically test a plurality of stimulation schemes until an evoked potential response is detected by the plurality of recording electrodes having a maximum response amplitude. Each said stimulation scheme of the general search mode includes assigning positions of the active electrodes and polarity of the active electrodes. The general search mode further comprises instructing the stimulator to ramp stimulation intensity of a stimulation during testing each said stimulation scheme until either a maximum stimulation intensity value is reached or the maximum evoked potential response amplitude is detected. The maximum evoked potential response amplitude is an evoked potential recording that does not increase in amplitude upon an increase in stimulation intensity. The stimulation scheme at which the maximum response amplitude is detected comprises a positive stimulation scheme.

In some embodiments, a system is configured to enhance diagnostic evoked potential recordings of a nerve or nerve pathway of interest. The system comprises a plurality of stimulating electrodes arranged in a grid array configured to be placed on, over, or through skin over an area that the nerve or nerve pathway of interest is suspected to lie beneath. The system comprises a stimulator configured to control the grid array. Each of the plurality of stimulating electrodes is independently assignable to be active or inactive. Each of the active electrodes is independently assignable to be an anode or a cathode. The stimulator is configured to independently assign stimulation parameters to each of the active electrodes. The system comprises a processor configured to automatically execute a focused search mode after the general search mode. The focused search mode comprises instructing the stimulator to systematically test a plurality of stimulation schemes until an evoked potential recording is detected by the plurality of recording electrodes having a maximum response amplitude and a minimum stimulation intensity. The focused search mode further comprises instructing the stimulator to ramp the stimulation intensity during testing each said stimulation scheme until the maximum response amplitude is detected. The focused search mode further comprises recording the stimulation intensity during testing each said stimulation scheme at which the maximum response amplitude is detected, comparing the stimulation intensities at which the maximum response amplitude was detected, and selecting the minimum stimulation intensity at which the maximum response amplitude was detected.

In some embodiments, a computer-implemented method for enhancing diagnostic evoked potential recordings of a nerve or nerve pathway of interest. The method comprises, by one or more processors executing program instructions, communicating with a stimulator configured to control a grid array of a plurality of stimulating electrodes, wherein: the plurality of stimulating electrodes are arranged in the grid array and configured to be placed on, over, or through skin over an area that the nerve or nerve pathway of interest is suspected to lie beneath, each of the plurality of stimulating electrodes is independently assignable to be active or inactive, each of the active electrodes is independently assignable to be an anode or a cathode, and the stimulator is configured to independently assign stimulation parameters to each of the active electrodes; automatically executing a general search mode and a focused search mode after the general search mode, the general search mode comprising instructing the stimulator to systematically test a plurality of stimulation schemes until an evoked potential response is detected by a plurality of recording electrodes having a maximum response amplitude, wherein the plurality of recording electrodes configured to record at least one of Somato-Sensory Evoked Potentials (SSEPs) and Transcranial Electrical Motor Evoked Potentials (TCeMEP), each said stimulation scheme of the general search mode including assigning positions of the active electrodes and polarity of the active electrodes, the general search mode further comprising instructing the stimulator to ramp stimulation intensity of a stimulation during testing each said stimulation scheme until either: a maximum stimulation intensity value is reached, or the maximum evoked potential response amplitude is detected, wherein the maximum evoked potential response amplitude is an evoked potential recording that does not increase in amplitude upon an increase in stimulation intensity, and wherein the stimulation scheme at which the maximum response amplitude is detected comprises a positive stimulation scheme, the focused search mode comprising utilizing information from the positive stimulation scheme to instruct the stimulator to systematically test the plurality of stimulation schemes until an evoked potential recording is detected by the plurality of recording electrodes having the maximum response amplitude and a minimum stimulation intensity, the focused search mode further comprising instructing the stimulator to ramp the stimulation intensity during testing each said stimulation scheme until the maximum response amplitude is detected, the focused search mode further comprising: recording the stimulation intensity during testing each said stimulation scheme at which the maximum response amplitude is detected, comparing the stimulation intensities at which the maximum response amplitude was detected, and selecting the minimum stimulation intensity at which the maximum response amplitude was detected; and using the minimum stimulation intensity at which the maximum response amplitude was detected to continually stimulate the nerve or the nerve pathway.

The general search mode further may comprise, after the evoked potential recording is detected, executing another stimulation scheme. The electrodes of the grid array may be spaced substantially evenly. The electrodes of the grid array may be arranged in aligned rows and columns having four corners. At least one of the general search mode and the focused search mode may comprise a stimulation scheme in which at least two corner positioned electrodes of the grid array may be assigned to be active electrodes. At least one of the general search mode and the focused search mode may comprise a stimulation scheme in which at least three corner positioned electrodes of the grid array may be assigned to be active electrodes. The grid array may comprise two rows and two columns. The grid array may comprise three rows and three columns. The grid array may comprise two rows and four columns. The grid array may comprise three rows and six columns. The grid array may comprise eleven rows and eleven columns. The grid array may comprise between two and fifty rows and between two and fifty columns. The grid array may comprise between 2 and 100 rows and between 2 and 100 columns. The grid array may comprise an odd number of rows and an odd number of columns. The grid array may comprise a first number of rows and a second number of columns, the second number being at least 2 times greater than the first number. The grid array may comprise a first number of rows and a second number of columns, the second number being at least 3 times greater than the first number. The grid array may comprise a first number of rows and a second number of columns, the first number being at least 2 times greater than the second number. The grid array may comprise a first number of rows and a second number of columns, the first number being at least 3 times greater than the second number. The electrodes of the plurality of electrodes may be percutaneous. The electrodes of the plurality of electrodes may be transcutaneous. The electrodes of the grid array may be arranged in a circular pattern. The circular pattern may comprise a ring and an electrode in the ring. At least one of the general search mode and the focused search mode may comprise a stimulation scheme in which at least two ring positioned electrodes of the grid array may be assigned to be active electrodes. At least one of the general search mode and the focused search mode may comprise a stimulation scheme in which at least three ring positioned electrodes of the grid array may be assigned to be active electrodes. At least one of the electrodes of the grid array may comprise an atraumatic tip. The atraumatic tip may comprise a spherical shape. The atraumatic tip may comprise a planar shape. The grid array may be configured to be placed on a limb. The grid array may be configured to be placed on a leg. The grid array may be configured to be placed on a thigh. The grid array may be configured to be placed on a calf. The grid array may be configured to be placed on a foot. The grid array may be configured to be placed on an arm. The grid array may be configured to be placed on an upper arm. The grid array may be configured to be placed on a forearm. The grid array may be configured to be placed on a hand. The grid array may be configured to be placed on a head. The plurality of recording electrodes may be configured to be placed on a head. The plurality of recording electrodes may be configured to be placed on a limb. The plurality of recording electrodes may be configured to be placed on a leg. The plurality of recording electrodes may be configured to be placed on a thigh. The plurality of recording electrodes may be configured to be placed on a calf. The plurality of recording electrodes may be configured to be placed on a fxoot. The plurality of recording electrodes may be configured to be placed on an arm. The plurality of recording electrodes may be configured to be placed on an upper arm. The plurality of recording electrodes may be configured to be placed on a forearm. The plurality of recording electrodes may be configured to be placed on a hand. The plurality of recording electrodes may be configured to be placed on a finger. The plurality of recording electrodes may be configured to be placed on a muscle. The grid array may be configured to be placed on a first appendage and the plurality of recording electrodes may be configured to be placed on a second appendage different than the first appendage. The grid array may be configured to be placed on a first limb and the plurality of recording electrodes may be configured to be placed on a second appendage different than the first limb. The stimulation parameters may be configured to inhibit at least one of discomfort and pain due to overstimulating with intensities that may be above the stimulation intensity. At least one of the stimulator, the general search mode, and the focused search mode may be configured to enhance a user's ability to acquire clinically useful evoked potentials in a nerve that may be technically challenging to stimulate due to at least one of anatomic positional variability, presence of disease, small caliber, edematous extremities, dry or scaly skin, or large body habitus. The grid array may comprise a plurality of smaller grid arrays each configured to stimulate multiple points along a course of the nerve or nerve pathway. The method may further comprise a safety button capable of being pressed by an awake subject to immediately stop the stimulation. The method may further comprise providing user controls configured to modify at least one of the general search mode and the focused search mode, the controls may comprise a limit on a total number of said stimulation schemes used. The limit on a total number of said stimulation schemes used may comprise two said stimulation schemes. The limit on a total number of said stimulation schemes used may comprise less than ten said stimulation schemes. The method may further comprise semi-automatically executing the general search mode and the focused search mode after the general search mode, wherein at least one of the general search mode and the focused search mode interruptible by a user. At least one of the general search mode and the focused search mode may be interruptible by a user visually monitoring the subject for unwanted side effect of the stimulation. The unwanted side effect of the stimulation may comprise patient movement. At least one of the general search mode and the focused search mode may be interruptible by a user monitoring maximum amplitudes recorded from a plurality of stimulation schemes that may be within a normal range of established normative data.

The plurality of recording electrodes may be configured to record Somato-Sensory Evoked Potentials (SSEPs). The SSEPs may provide a user with a continuous functional assessment of the nerve or nerve pathway during a procedure in which the nerve or nerve pathway may be known to be at risk of damage. The SSEPs may comprise at least one of peripheral nerve SSEP recordings, spinal SSEP recordings, subcortical SSEP recordings, and cortical SSEP recordings. During testing at least one said stimulation scheme, the stimulation may comprise a monophasic rectangular pulse having a duration between 100 μs and 1,000 μs and/or a maximum stimulation intensity between 30 mA and 60 mA. During testing each said stimulation scheme, the stimulation may comprise a monophasic rectangular pulse having a duration between 100 μs and 1,000 μs and/or a maximum stimulation intensity between 30 mA and 60 mA. The stimulation may comprise a repetition rate between 3 stimulations per second and 11 stimulations per second. The general search mode may comprise testing at least one of the plurality of stimulation schemes a plurality of times and determining a mean average of any evoked potential recordings for said at least one stimulation scheme. The plurality of times may comprise between about 100 times and about 1,000 times dependent on the signal to noise ratio. The nerve or nerve pathway may be a sensory nerve or sensory nerve pathway. The sensory nerve or sensory nerve pathway may comprise at least one of an ulnar nerve, a median nerve, a radial nerve, a musculocutaneous nerve, an antebrachial cutaneous nerve, a lateral femoral cutaneous nerve, a pudendal nerve, a femoral nerve, a sciatic nerve, a posterior tibial nerve, a peroneal nerve, a saphenous nerve, and a sural nerve. A location of damage risk to the nerve or nerve pathway may be between the grid array and the plurality of recording electrodes.

The plurality of recording electrodes may be configured to record Transcranial Electrical Motor Evoked Potentials (TCeMEP). The TCeMEPs may provide a user with a functional assessment of the nerve or nerve pathway during a procedure in which the nerve or nerve pathway may be known to be at risk of damage. The nerve or nerve pathway may be a motor nerve or motor nerve pathway. The grid array may comprise scalp electrodes configured to be placed at locations overlying a primary motor cortex to evoke responses in descending corticospinal motor tracts. The grid array may be configured to be positioned proximate to scalp positions C1, C2, C3, C4, Cz, or Fz as defined by the 10-20 System of the American Electroencephalographic Society. The method may further comprise a muscle recording channel configured to record an electromyographic reading from at least one muscle. The method may comprise a plurality of multiple muscle recording channels including the muscle recording channel, the plurality of muscle recording channels configured to record an electromycraphicn readon from at least one of upper extremities, lower extremities, head, and trunk. At least one of the general search mode or the focused search mode may further comprise sequentially evaluating the plurality of stimulation schemes for their ability to evoke a electromyographic muscle response or M response. During testing at least one said stimulation scheme, the stimulation may comprise a rapid train of electrical stimulus pulses having a pulse duration between 25 μs and 75 μs, a number of pulses between 3 and 8, and/or inter-pulse intervals between 2 ms and 4 ms. During testing each said stimulation scheme, the stimulation may comprise a rapid train of electrical stimulus pulses having a pulse duration between 25 μs and 75 μs, a number of pulses between 3 and 8, and/or inter-pulse intervals between 2 ms and 4 ms. At least one of the general search mode and the focused search mode may further comprise using the stimulation scheme and the minimum stimulation intensity at which the maximum response amplitude was detected in a TCeMEP monitoring mode. The TCeMEP monitoring mode may comprise monitoring TCeMEPs over a duration to provide a continuous near real time assessment of motor nerves and motor pathways. The monitoring mode allows a user to select use of a selected stimulation scheme yielding a response in a neuromuscular distribution of interest as the stimulation scheme in the monitoring mode. A location of damage risk to the nerve or nerve pathway may be between the grid array and the plurality of recording electrodes.

The plurality of recording electrodes may be configured to record Compound Muscle Action Potentials (CMAPs). The CMAPs may provide a user with a functional assessment of the peripheral motor nerve function. At least one of the general search mode and the focused search mode may further comprise detecting a stimulation intensity at which the stimulation produces a CMAP amplitude that does not increase with increasing stimulation intensity. The method may further comprise performing an independent search mode to provide an assessment of peripheral nerve motor function for segments of nerves and to acquire CMAP recordings from at least two separate sites at a known distance apart to calculate nerve conduction velocity. The plurality of recording electrodes may comprise an active electrode on a belly of the muscle of interest, a reference electrode between 2 cm and 10 cm away from the active electrode and on the tendon or a nearby electrically inactive region, and a ground electrode configured to reduce artifact effects of the stimulation. The stimulation intensity may be between 1 mA and 60 mA and/or have a pulse duration between 0.05 ms and 0.2 ms. A location of damage risk to the nerve or nerve pathway may be between the grid array and the plurality of recording electrodes.

The plurality of recording electrodes may be configured to record Sensory Nerve Action Potentials (SNAPs). The SNAPs may provide a user with a functional assessment of the peripheral sensory nerve function. At least one of the general search mode and the focused search mode may further comprise detecting a stimulation intensity at which the stimulation produces a SNAP amplitude that does not increase with increasing stimulation intensity. The plurality of recording electrodes may comprise an active electrode, a reference electrode between 2 cm and 10 cm away from the active electrode, and a ground electrode configured to reduce artifact effects of the stimulation. The method may further comprise performing an independent search mode to provide an assessment of peripheral nerve motor function for segments of nerves and to acquire SNAP recordings from at least two separate sites at a known distance apart to calculate nerve conduction velocity. The stimulation intensity may be between 1 mA and 60 mA and/or have a pulse duration between 0.05 ms and 0.2 ms. A location of damage risk to the nerve or nerve pathway may be between the grid array and the plurality of recording electrodes.

The plurality of recording electrodes may be configured to record Mixed Nerve Action Potentials (MNAPs). The MNAPs may provide a user with a functional assessment of the peripheral mixed nerve function. At least one of the general search mode and the focused search mode may further comprise detecting a stimulation intensity at which the stimulation produces a SNAP amplitude that does not increase with increasing stimulation intensity. The plurality of recording electrodes may comprise an active electrode, a reference electrode between 2 cm and 10 cm away from the active electrode, and a ground electrode configured to reduce artifact effects of the stimulation. The method may further comprise performing an independent search mode to provide an assessment of peripheral nerve motor function for segments of nerves and to acquire MNAP recordings from at least two separate sites at a known distance apart to calculate nerve conduction velocity. The stimulation intensity may be between 1 mA and 60 mA and/or have a pulse duration between 0.05 ms and 0.2 ms. A location of damage risk to the nerve or nerve pathway may be between the grid array and the plurality of recording electrodes.

BRIEF DESCRIPTION OF THE DRAWINGS

FIG. 3 illustrates the hypothetical spatial distributions of current densities that might be produced surrounding the grid (1) illustrating how the current distributions might present differently with four different stimulation schemes (variations of active electrodes on the grid). The current density produced from a brief burst of stimulation using each stimulation scheme may or may not be sufficient to activate a nearby nerve (6) and concurrent differential amplification recordings (60) can be analyzed and observed on a display (40). In this diagram, higher current densities are designated with progressively darker color and lower current densities are designated with progressively lighter colors as shown in the key. The electrode polarity designations are labeled with a negative sign for cathodes and a plus sign for anodes. All electrodes on the grid without polarity designations may be considered as electrically inactive.

FIG. 4 illustrates hypothetical spatial distributions of current densities that might be produced surrounding the grid (1) using four additional stimulation schemes. FIG. 4 illustrates how certain stimulation schemes may offer advantages over other schemes. In this example, the intensity of stimulation to obtain the maximum amplitude evoked potential response is lowest with scheme 8 which may only utilize 7 mA of stimulation intensity to elicit the maximum amplitude evoked potential response versus scheme 7 or scheme 6 which may utilize 9 mA and 10 mA respectively to elicit the maximum amplitude evoked potential response.

FIG. 5 illustrates examples of the hypothetical spatial distribution of current densities that might be produced using a larger grid with a greater number of electrodes (41). In this example the grid (41) has 11 columns and 11 rows of equidistantly spaced electrodes. Stimulation schemes 1 and 2 show how multiple adjacent electrodes can be assigned the same polarity for a cumulative effect on the spatial distribution of current density to create a larger spatial distribution of current density in a particular region of the grid. In schemes 1 and 2, multiple cathodes are activated simultaneously in opposite quadrants of the grid to create a spatial distribution of current density that might be useful for "scanning" quadrants of the grid, searching general regions of the grid for evoked potential responses. Schemes 3 and 4 illustrate additional examples of how multiple adjacent electrodes can be designated with the same polarity to produce specific spatial distributions of current densities. Schemes 3 and 4 illustrate more examples of how the software might employ relatively larger, more generalized spatial distributions of current density which may be useful to scan the grid and help to detect and localize the presence of evoked potential responses to a particular side or quadrant of the grid and guide subsequent stimulations towards the goal of obtaining the optimal configuration of active electrodes and stimulation parameters which yield the highest quality evoked responses while using the lowest amount of stimulation intensity.

FIG. 10 illustrates the hypothetical current densities that might be generated surrounding the circular electrode (100) with a simple clockwise sequence activating electrodes in a bipolar configuration in a 360-degree sweep with each stimulation having the cathode and anode positioned 180 degrees directly across from one another. In this example a peripheral nerve (6) that is to be studied is located near the electrode.

FIG. 11 illustrates the circular electrode (100) with a simple clockwise sequence of multi-polar stimulation utilizing a central cathode surrounded by 2 anodes along with the hypothetical current densities that would be produced with each of 8 sequential stimulations with the cathode switching to 1 position in the clockwise direction on each successive stimulation.

DETAILED DESCRIPTION

Figure 1:
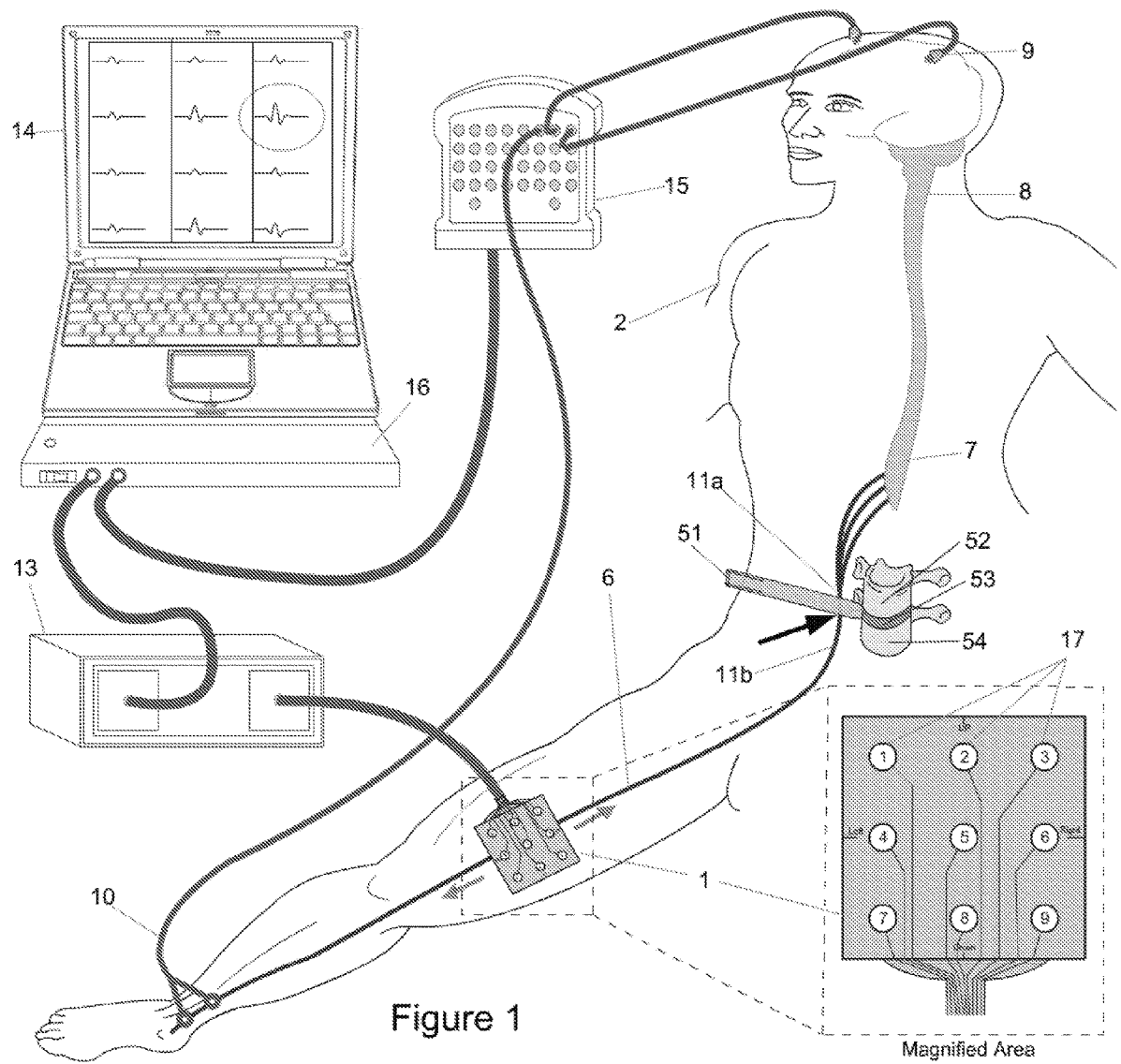
FIG. 1 illustrates the basic components of a particular embodiment of these materials and methods in a system designed for the purpose of intraoperative monitoring of the femoral nerve (11a proximal segment and 11b distal segment) via stimulation of the femoral nerve's sensory extension—the saphenous nerve (6). It is suspected that expansion of surgical retractors (51) may stretch or compress the femoral nerve at the surgical site (black arrow). To perform the discectomy and fusion procedure, a surgical corridor may be established from the skin to the access the L4-L5 disc space (53) between the L4 vertebrae (52) and L5 vertebrae (54). The surgical retractors (51) may traverse through the psoas muscle (not shown) to reach the disc space and they come in close proximity to the lumbar plexus and particularly the femoral nerve (11a and 11b). In this embodiment, a stimulating grid electrode system (1) with multiple electrodes (17) is placed on the right leg of a patient (2) in an area of the skin where the nerve to be stimulated (6) is suspected to lie directly under. The grid is powered by an external multi-channel electrical power source (13) with electrical output that is precisely controlled by specifically designed software/computer system/display (14). The power source is designed to deliver brief pulses of precisely controlled current to each electrode on the grid independently. Following each individual pulse of stimulation delivered to the grid, the system utilizes recording electrodes (9, 10) placed over appropriate distant neural elements or muscles (not shown) to detect any elicited evoked potential responses using a differential amplification system (16). The differential amplification system which may include a pre-amplifier (15) that amplifies and digitizes differential recordings from various recording electrodes along the neural pathway or a muscle. In this particular embodiment, evoked response recordings may be acquired from neural activity in the cerebral cortex (9), cervical spine (8), spinal cord (7) or peripheral nerve (10). Following each individual stimulation of the grid, the system records a brief period of time (e.g., possibly ranging from approximately 10-200 milliseconds (ms or msec)) and mathematically analyzes the recordings using algorithms designed to detect and analyze any evoked potential responses generated from electrical stimulation of the grid.

FIG. 1 illustrates an example of how these materials and methods can be utilized in a specific application for optimizing intraoperative saphenous nerve sensory evoked potential recordings for femoral nerve monitoring during a surgical procedure which femoral nerve is known to be at risk. In this example, the surgical procedure is a right L4-L5 trans-psoas retroperitoneal interbody discectomy and fusion procedure. In this particular embodiment in FIG. 1, a multipolar grid electrode array (1) with multiple numbered electrodes (17), is placed on the right medial thigh of the patient (2) across an area of skin where the saphenous nerve (6) is suspected to be located beneath. The grid electrode (1) has 3 equidistantly spaced rows and columns of electrodes to produce a 9 electrode square grid. This embodiment is only a single simple example of an electrode array and any number any type of electrodes on the grid can be utilized. Different applications will utilize differences in the material design including different numbers of electrodes on the grid, different types of electrodes on the grid and different electrode spacing, all depending on the specific application. Electrodes can be surface electrodes that do not penetrate the skin or they can be more invasive needle electrodes that might be designed to penetrate the skin and deliver more focal stimulation to deeper nerves such as the case in the main example provided herein.

A software/computer system (14) integrates the precise delivery of brief pulses of electrical current (referred to as "stimulations") from an electrical power source (13) with the capability to deliver precise amounts of current and independently to each particular electrode (17) on the grid (1). For any given stimulation, each electrode can be designated with a polarity as an anode, cathode or rendered electrically inactive. The software recognizes the position of each electrode on the grid and each electrode can be designated with a descriptive label that describes its location on the grid such as the electrode's row and column. The software/computer system (14) is integrated with a differential amplification system for detecting, recording and analyzing any evoked potential response following each individual pulse of stimulation to the grid. The differential amplification system might include a pre-amplifier (15) that digitizes the analog recordings from multiple channels that are fed into a differential amplification base unit (16) for processing. The software/computer system directs sequences of stimulations by controlling the output of the power source to each electrode on the grid. The system can alter the configuration of active electrodes on the grid and the stimulation parameters for subsequent stimulations based on information that is obtained from the mathematical analysis of differential amplification recordings from prior stimulations. The system systematically analyzes multiple recordings for multiple variations of electrode configurations and searches for the optimum stimulation configuration and parameters that yield the highest quality evoked potential responses using the least amount of stimulation intensity. Multiple similar stimulations with the same stimulation configurations and/or parameters might be utilized sequentially to apply signal averaging techniques as are commonly utilized in sensory evoked potential recording techniques that will help to resolve evoked potentials that may have a low signal to noise ratio.

If stimulation with a particular configuration of active electrodes on the grid (1) delivers sufficient electrical current in proximity of the saphenous nerve (6), the induced current density can activate the peripheral nerve axons by causing opening of voltage-dependent transmembrane ion channels resulting that can induce a traveling nerve action potential in both directions; orthodromically and antidromically (small grey arrows). The resultant traveling action potentials can be recorded with various electrodes connected into a pre-amplifier (15) that is connected to a multi-channel differential amplification system (16). The recording electrodes can be placed at various sites along the nerve and/or neural pathway where the traveling impulses can be recorded. In this example, stimulation of the saphenous nerve in the distal medial thigh activates the sensory nerve axons which sends evoked potentials that travel proximally towards the brain, traversing through the femoral nerve distal to the site of the surgery (11b), across the site of the surgery (large black arrow), through the proximal portion of the femoral nerve (11a), and onto the spinal cord and brain. Standard subdermal recording electrodes can be utilized to capture the sensory evoked responses at proximal sites such as the lumbar spine (lumbar potentials) (7), the cervical spine (cervical potential) (8) and cerebral cortex (cortical responses) (9) using standard somatosensory evoked potential recording techniques. In this example, an evoked potential responses may also be recorded from the distal portion of the peripheral nerve such as the most distal part of the saphenous nerve at the medial ankle (10). Recording from a distal site may be helpful by providing confirmation that the nerve has been adequately activated which can be helpful information to rule out a technical problem with the stimulation system. The valuable recordings for monitoring femoral nerve function in this example are the proximal recordings because the traveling nerve impulses had to traverse through the surgical site where the nerve is at risk (in this example 7, 8, 9 and 10). Continuously recording an evoked response from a site that is proximal to the site of the surgery where the nerve is at risk can provide important information that the nerve pathway is functioning. Such a functional assessment can provide important feedback during a surgery regarding the ongoing functional status of the nerve at risk over time. In the surgical procedure in this example, a surgical corridor may be established from the skin on the patient's right lower flank to access the L4-5 disc space (53) between the L4 vertebrae (52) and L5 vertebrae (54) using sequential tissue dilation and surgical retraction. Surgical instrumentation such as a retractor (51) can create direct or indirect strain on the femoral nerve (11a and 11b) or related vasculature at the site of the surgical retraction (large black arrow). Continually recording evoked responses can be helpful for detecting any negative effects on nerve function which may be caused by the surgical procedure itself. When nerve function begins to fail it is suspected that corrective actions can be taken in a timely manner to avoid permanent iatrogenic neurological injury (for example, removal of the surgical retraction and allowing time for the nerve to recover and return to functioning) (Chaudhary et al).

The system delivers consecutive individual brief pulses of current to particular configurations of electrodes on the grid referred to as "stimulations". The purpose is to activate the nerve of interest (6) so that evoked potentials can be recorded and analyzed. Each individual pulse of stimulation delivered to the grid will be associated with a particular stimulation "scheme". A stimulation scheme is defined by the pattern of active and inactive electrodes on the grid as well as the stimulation parameters utilized. Active electrodes are designated with a stimulus polarity as either a cathode or anode. Stimulation of any particular scheme may be applied with specific stimulation parameters which are precisely controlled by the system. Stimulation parameters may include stimulus duration, stimulus intensity, pulse shape, number of pulses, inter-pulse intervals, monophasic or biphasic, balanced or unbalanced charges, constant current or constant voltage or other characteristics that describe the electrical stimulation. Particular stimulating parameters can be tailored to each particular application. For example, stimulation parameters might comprise a brief delivery of a square wave pulse of current with a stimulus duration ranging from 50-1000 microseconds with an intensity ranging from 0.10-100 milliamps.

The system uses a differential recording amplifier to detect and analyze any resultant evoked potential activity following each individual stimulation of the grid. For example, the system might analyze the information obtained from the first 100 milliseconds of differential amplification following each burst of stimulation. Analog differential recordings are digitized and analyzed for the presence of evoked potential responses and mathematical analysis is applied to the resultant waveform characteristics. The main waveform characteristic commonly utilized to assess evoked potential responses is amplitude, however the mathematical analysis of the evoked potential responses may include analysis of additional waveform morphology characteristics that may be useful in choosing the most useful and stable evoked potential responses. The additional waveform characteristics might include latencies, waveform duration, phase analysis, area under the curve and analysis of the waveform slopes. In addition there may be other mathematical measures that may be found to be useful to assess the evoked potential quality and consistency over time.

In this embodiment, the amplitude and other characteristics of the saphenous sensory evoked potential waveform morphologies from each successive stimulation of the grid (1) can be mathematically analyzed by the software and the waveforms and results of the mathematical analysis can be visually observed by an operator on a display (14). The system is designed to sequentially deliver bursts of stimulation to variable stimulation schemes and evaluate the results. The software mathematically analyzes and evaluates the recordings from each individual stimulation of the grid and directs the power source to deliver specific subsequent patterns and parameters of current output to the grid to target the optimal stimulation schemes which yield the highest quality of evoked potential recordings while utilizing the lowest amount of current. One main goal of the system is to determine the most efficient stimulation scheme that yields the highest quality evoked potential responses.

Figure 2:
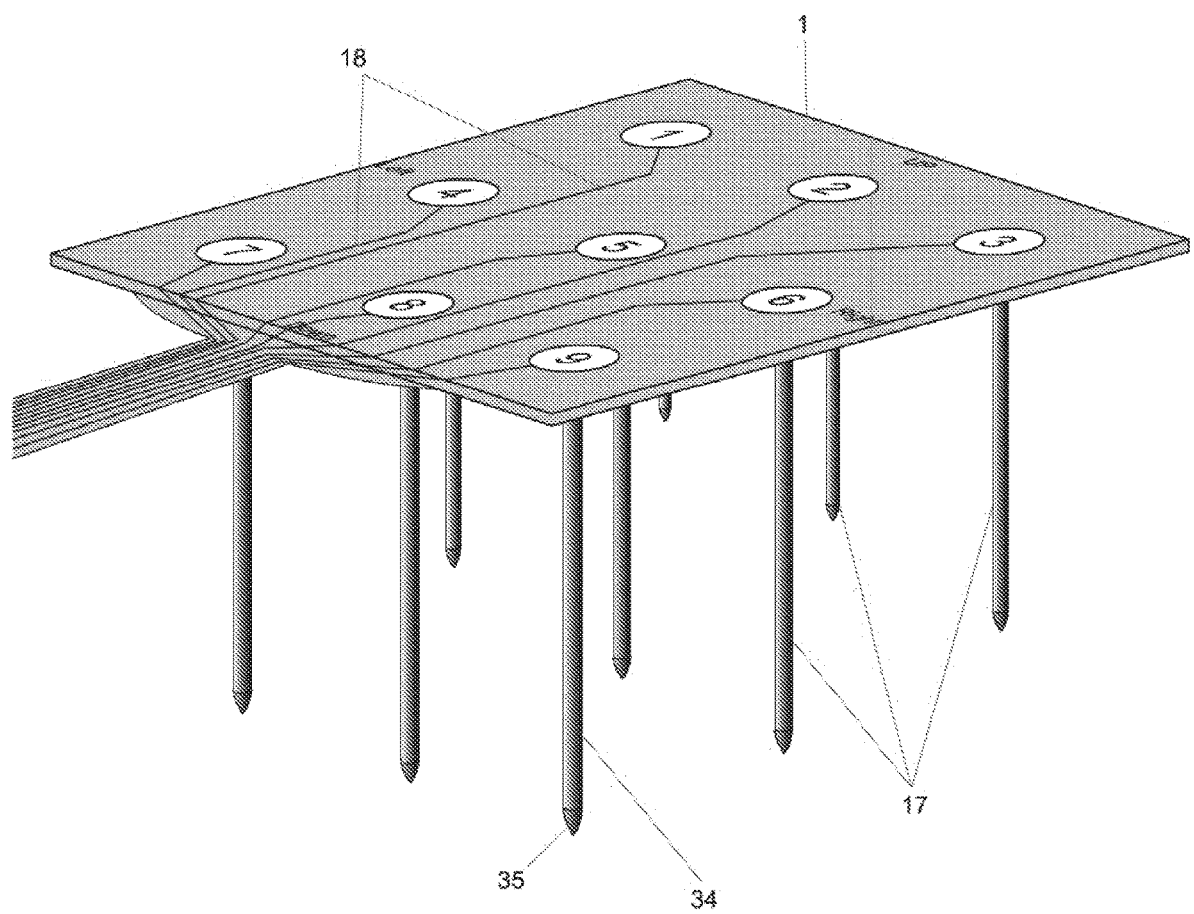
FIG. 2 illustrates an oblique view of a particular embodiment of a stimulating electrode grid (1) with independent electrical wiring connections (18) to each of the nine needle electrodes (17) that are equidistantly arranged in this example of a simple 3×3 grid. Each needle electrode may have an electrically insulated shaft (34) with an uninsulated tip (35) to ensure focal electrical current is delivered in proximity to the deep nerve. The system designates each electrode with a number or alphanumeric label that designates its relative position in the grid. In this particular example the electrodes are numbered 1 through 9.

FIG. 2 shows the same electrode grid (1) from FIG. 1 from an oblique angle which illustrates an example of a specific design with lengthy needle electrodes that might be utilized to stimulate a deep nerve such as the saphenous nerve as seen in the example shown in FIG. 1. FIG. 2 is an example of a square grid comprising 3 equidistantly spaced rows and columns of needle electrodes for a total of 9 electrodes (17) on the grid (1). Each electrode is independently wired (18) and connected to the electrical power source (13) that is controlled by software that can deliver precisely controlled pulses of current to each electrode on the grid independently. The electrodes in this particular example (17) have an electrically insulated shaft (34) with an uninsulated tip (35) where concentrated current is emitted. This type of grid is specifically designed to penetrate the skin and deliver deep focal electrical stimulation at a closer range to a deep nerve. Different needle electrode diameters, lengths and shapes may be utilized for different applications. It might be found to be advantageous to choose an electrode size and shape for each particular patient. For accessing deeper nerves, it may be found that the needle size and shape could be specifically tailored for each particular patient and might be determined based on estimations from anthropometric measurements or electrode sizing may be determined even more accurately from measurements obtained from pre-operative imaging studies such as MRI or CAT scans. In the case where deep nerve stimulation is desired, strategically sizing the electrodes may improve the proximity of current delivery to the nerve, resulting in a higher rate of successfully obtaining useful evoked potential responses and a reduction in the stimulation current to obtain optimal evoked responses.

FIG. 3 illustrates the concept of how different electrode stimulation schemes might produce different spatial distributions of current densities in biological tissues following stimulation using a grid electrode system such as the one shown in FIGS. 1 and 2. FIG. 3 illustrates four different stimulation schemes and the hypothetical spatial distributions of current densities that they might produce. The key in the middle of FIG. 3 shows how to read the diagram and other diagrams to follow. A negative sign is used to designate a cathode while a positive sign designates an anode. Electrodes without a positive or negative designation are considered "inactive" in that particular scheme. The key designates a volume of biological tissues with relatively greater current density as darker and less current density as lighter. Current density is typically measured in amperes per square meter A/m2. FIG. 3 illustrates how greater current density is expected to be greatest in close proximity to the cathode with significantly diminishing current densities at increasing distance away. Current density is expected to decrease rapidly at increasing distance away from the current source. The shapes of the current density spatial distributions in the diagrams are only hypothetical estimates for the purpose of illustrating the basic concepts of how current density spatial distributions in biological tissue might present following electrical stimulation with the assumption that the biological tissue has a homogenous electrical conductance. In reality, biological tissue does not have a homogenous electrical conductance as different biological tissue elements have different electrical conductance that will alter the morphology of the distribution of current and the actual spatial distribution of the current densities in heterogeneous biological tissues will differ. Nonetheless, this fact should not prevent this system from achieving one of its' main goals; to determine the stimulation scheme(s) and parameters that yield optimum evoked potential responses. Regardless of variable tissue electrical conductance and non-homogenous spatial distributions of current density in biological tissues, theoretically, there should be an optimal configuration of active electrodes and stimulation parameters that will yield the highest quality evoked responses while utilizing the least amount of electrical stimulation intensity.

In the search mode, various stimulation schemes are sequentially employed for the system to systematically search for the optimal configuration and stimulation parameters. Each scheme can be stimulated multiple times at the same stimulation intensity and parameters or the stimulation intensity can be sequentially increased in successive stimulations of the same scheme until either a maximized evoked potential response is detected or the stimulation intensity reaches a predetermined maximum level. Certain stimulation schemes might result in a spatial distribution of current in close enough proximity to the nerve (6) to electrically activate the nerve axons and evoke a recordable action potential (FIG. 3 scheme 4) while other stimulation schemes may not produce a current spatial distribution that is sufficient to activate the nerve (FIG. 3 schemes 1,2 & 3). Stimulation schemes that produce a spatial distribution of current density sufficient to activate neural structures can evoked a response (60) that can be recorded, analyzed and displayed with standard differential amplification systems and methods and displayed on a monitor (40). In the main example in this publication, sensory evoked potentials are being recorded. It is well known that sensory evoked potentials (for example, using scalp recording electrodes to detect cortical sensory activity) are likely to have a low signal to noise ratio. In the case of recording cortical sensory evoked potentials from peripheral nerve stimulation, it is likely that signal averaging techniques may be utilized and multiple similar stimulations may be utilized for each particular stimulation scheme. These repeated stimulations can be averaged over time in order to discern the "time locked" cortical evoked potential response of interest and minimize the contribution of random noise to the recordings.

The number of averages used to resolve an evoked potential response will vary depending on multiple factors, especially the signal to noise ratio. In other applications where the signal of interest has a higher signal to noise ratio, signal averaging will likely not be used. For example, in cases where these materials and methods are applied to stimulating motor nerves using muscle electromyographic activity (EMG) recordings as the evoked response of interest, averaging techniques will likely be unnecessary due to the relatively high signal to noise ratio. When signal averaging is used, the system may utilize mathematical algorithms to determine the number of averages used to consider an evoked response to be adequately resolved such as a diminishing return of increasing amplitude or other mathematical measures that might suggest that the signal of interest has been averaged adequately and additional stimulations will not yield a significant improvement in the recorded responses. In situations where many stimulations are used to discern an evoked potential response, it will increase the time for the system to complete a scan and determine the optimal stimulation configuration and parameters. The speed at which the system can deliver successive bursts of stimulation with be limited by the repetition rate. The repetition rate is defined as the number of individual stimulations delivered per second. The maximum repetition rate at which the system will be permitted to deliver successive stimulations will be limited by biological factors including the nerve refractory period as well as electrical safety restrictions that might be related to the total charge delivered or limited by other safety concerns such as tissue heating. It is suspected that successive stimulations might be delivered at a repetition rate ranging from approximately 2-7 stimulations per second which should be sufficient to ensure that the stimulation does not deliver stimulation overlapping during the absolute or relative refractory periods of the nerve. Thus, assuming that the stimulation rate and stimulation parameters does not exceed electrical safety restrictions, the system should be able to complete a scan of the grid and hone in on the optimal stimulation scheme in an acceptable amount of time. The actual time the system takes to complete a scan in any given situation is unknown and will depend on multiple factors, especially the signal to noise ratio of the evoked potential of interest. For discerning low signal to noise ratio evoked potentials, it is estimated that the system should be able to sample approximately 5-7 stimulations per second, which would result in the analysis of 300-420 stimulations per minute. For example, in the main example herein where the system is designed for optimization of cortical sensory evoked potentials used for intraoperative monitoring, recordings will likely use signal averaging techniques utilizing multiple sequential stimulations of each individual scheme. Nonetheless, in is suspected that in most cases, the time to complete a scan and obtain optimal cortical sensory evoked potentials may be within acceptable limits. For example, if the system uses 1000 separate stimulations of various schemes to complete a scan, at a rate of 5 stimulations per second it will take approximately 3.5 minutes to complete the scan. This length of time may be perfectly acceptable for applications such as intraoperative monitoring where evoked potential recordings are optimized at baseline and then performed over the course of a procedure which might be several hours in duration. Even in this example where it may take 3.5 minutes to determine the optimal stimulation characteristics at the beginning of the surgical procedure, it may be quite beneficial to ensure optimized evoked potential recordings that will help to monitor nerve function over the remaining hours of the surgical procedure.

FIG. 3 shows hypothetical examples of the different effects on the spatial distribution of current density following stimulation using four different stimulation schemes. This particular system is designed to elicit evoked potentials from the nerve of interest (6) which, in this example, is crossing underneath the grid electrode (1) at an oblique angle. Each individual scheme may be stimulated multiple times with the same stimulation intensity and parameters (for signal averaging purposes) or stimulated with sequentially increasing stimulation intensity that will terminate when either a maximum amplitude evoked response is obtained (e.g., additional stimulation intensity no longer increases the amplitude of the evoked potential response) or the stimulation intensity reaches a pre-determined maximum level. In the examples provided herein, the maximum stimulation intensity is set arbitrarily to 15 milliamps. The maximum acceptable stimulation intensity will depend on multiple factors and can be set by the operator (as long as they are within the defined limits of electrical safety). The setting for the maximum stimulation intensity for a given application might be pre-determined by various methods such as mathematical estimates of total current delivery, experimental methods such as those that measure current densities in biological tissues or other methods that might simply include experience using a working system. For example, it may be found that in scan mode, the system may only increase the stimulation intensity of each scheme up to a maximum intensity of 10 milliamps in order to determine the most optimal stimulation scheme(s). The software may ensure that the total charge output is limited to within electrical safety limits. There are also temporal constraints that limit the frequency of successive stimulations (repetition rate) which may be considered to ensure the activated nerve axons have time to recover from between successive stimulations (refractory periods). The software may also be integrated with additional safety mechanisms. For example, a feedback system can be implemented that can automatically shut off the stimulation when input from accelerometers indicate that the stimulation has induced patient movement. Other types of safety mechanisms may also be found to be useful such as temperature gauges placed in proximity to the stimulation site that ensure that successive stimulation does not damage tissues from excessive heating.

FIG. 3 scheme 1 is an example of a multipolar scheme with electrode #1 on the grid designated as the cathode and electrodes #3 and #7 are designated as anodes. This combination of electrically active electrodes produces a particular distribution of current densities in the biological tissues surrounding the electrodes as illustrated by the current density diagram key in the middle of the FIG. 3. In FIG. 3 scheme 1, stimulation does not elicit a detectable evoked potential response even when the stimulation intensity is increased to the maximum predetermined level of 15 milliamps (mA). The spatial distribution of current density created from maximal stimulation of scheme 1 does not produce any appreciable current density in proximity of the nerve of interest (6) and no evoked potential responses are detected as shown on the monitor (40). FIG. 3 scheme 2 is also a multipolar scheme, but it has an active electrode configuration with a single cathode designated to the electrode #5 (the central electrode of the grid) with two electrodes designated as anodes on both sides diagonally at electrode positions #3 and #7. Similar to scheme 1, stimulation of scheme 2 (up to the maximum stimulation level of 15 mA) does not produce current density in the proximity of the nerve of interest (6) and thus no evoked potential responses are observed. FIG. 3 scheme 3 is an example of a bipolar scheme with a single cathode designated to electrode #7 and a single anode designated to electrode #3. Maximal stimulation of scheme 3 at 15 mA also does not create a sufficient current density in proximity to the nerve and no evoked potential responses are elicited. FIG. 3 scheme 4 is also a bipolar scheme with a single cathode designated to electrode #1 and a single anode designated to electrode #9. Maximal stimulation of scheme 4 at the stimulation limit of 15 mA produces a low amplitude evoked potential response. In scheme 4, at a stimulation intensity of 15 mA, a sufficient current density is produced in proximity to the nerve which is sufficient to activate a small portion of the total number of axons that make up the peripheral nerve resulting in a low amplitude evoked potential response (60) as shown on the monitor (40).

FIG. 4 illustrates four more examples of stimulation schemes and how the current densities they produce can be markedly different from one another. FIG. 4 scheme 5 is an example of a diagonal bipolar scheme with a single cathode designated to electrode #3 and a single anode designated to electrode #7. Maximal stimulation of scheme 5 at 15 mA does not create a sufficient current density in proximity to the nerve and no evoked potential responses are elicited. FIG. 4 scheme 6 is also a diagonal bipolar scheme with a single cathode designated to electrode #9 and a single anode designated to electrode #1. Stimulation with this scheme results in a high current density in proximity to the nerve and a maximal amplitude evoked potential response is obtained at 10 mA. In this example, the system has detected that stimulation intensity greater than 10 mA does not further increase the amplitude of the evoked potential response any further and thus it is concluded that the axons of the nerve have been activated. Once the maximum amplitude of the evoked potential response is detected, the addition of a higher intensity of stimulation would not offer any benefit in improving the evoked potential responses and would only be detrimental. As a particular scheme is stimulated sequentially with increasing stimulation intensity, the system will detect the point when the maximum evoked potential response amplitude is achieved and evaluate the stimulation intensity at which maximum amplitude responses are achieved. FIG. 4 scheme 7 is a multi-polar scheme with electrode #9 on the grid designated as the cathode and electrodes #3 and #7 are designated as anodes. Scheme 7 also produces a relatively high current density in proximity to the nerve sufficient to elicit evoked potential responses. In this hypothetical example, the maximum amplitude evoked potential response with this particular scheme is obtained with a stimulation intensity of 9 mA. The system is programmed to evaluate and compare the results of each stimulation. In this example, the system would mathematically determine that that scheme 7 uses less stimulation intensity to reach the maximum response amplitude than scheme 6.

FIG. 4 scheme 8 is also a multi-polar scheme with electrode #9 designated as the cathode and electrodes #6 and #8 are designated as anodes. In this hypothetical example, scheme 8 produces a more focal current distribution compared to the prior examples and the maximum evoked potential response is obtained with a stimulation intensity of only 7 mA. The system would recognize that scheme 8 uses less stimulation intensity than schemes 1 through 7 to achieve a maximum evoked potential response amplitude. In this example, scheme 8 could be considered the most optimal stimulation scheme that yields the highest quality evoked response while using the least amount of electrical stimulation intensity.

The process of finding the optimal scheme and parameters can be referred to as "scanning" and the system can be said to be in "scan mode" as it systematically progresses through variable sequential stimulation schemes of the grid to determine the optimal stimulation scheme and parameters. The specific instructions for the mathematical programming of the software for scan mode is not outlined herein, however is should be evident how the system can be programmed to mathematically analyze the results of successive epochs of differential amplification recordings from various stimulation schemes. A key feature is that the system will have the ability to guide the choice of subsequent stimulation schemes based on the mathematical analysis of prior stimulations so that the system is designed to systematically determine the most effective schemes that produce the maximum amplitude evoked potential responses while utilizing the least amount of electrical stimulation intensity.

In Scan Mode, the software will determine the optimal stimulation scheme using programmed mathematical algorithms that will choose the pattern and parameters of subsequent stimulation schemes based on the information gained from recordings from prior stimulation schemes. Scan mode will be programmed to systematically search the grid for evoked potential responses, likely beginning with a scan protocol that initially scans broad sections of the grid and then becomes more focused, directing subsequent stimulations to more focal areas of the grid based on the information acquired. Once evoked potentials are detected in a general area of the grid, the system can employ progressively more focal stimulation schemes for analysis. The goal of search mode will be to the efficiently calculate the optimal stimulation scheme and stimulation parameters that yield the highest quality evoked potentials. Scan mode will be programmed to efficiently calculate the optimal stimulation scheme using the least amount of consecutive trial stimulations.

FIG. 5 illustrates a larger square grid system with a greater number of electrodes (41). Larger grid sizes with a greater number of electrodes can increase the resolution of the system however they also add greater complexity to the system and likely higher production costs. This example shows a grid with 11 rows and 11 columns. This example shows how the beginning of scan mode might contain more general stimulation schemes designed to scan general regions of the grid with schemes that are designed to detect the presence of evoked potentials from general areas of the grid. For example, a square grid such as the one in FIG. 5 can be broken down into 4 equal quadrants (as designated with the vertical and horizontal lines on the grid. In the grid in FIG. 5, quadrant 1 would include rows 1-6 that include columns A-F, quadrant 2 would include rows 1-6 that include columns F-K, quadrant 3 would include rows 6-11 that include columns A-F and quadrant 4 would include rows 6-11 that include rows F-K. The scan mode may begin with a generalized search of each quadrant. Once evoked responses are detected in a particular quadrant, a more focused search within that quadrant can be performed. Quadrants can be further broken down into sub-quadrants which might be systematically scanned in a similar fashion. This example illustrates how the software can be programmed with strategic sequential stimulations aimed at systematically honing in on the optimal stimulation configuration and parameters.

In FIG. 5, scheme 1 illustrates a particular scheme where there are three electrodes that are designated as simultaneous cathodes in the left upper corner of the grid (electrodes A1, A2 and B1 designated as cathodes). This scheme is an example of a scheme where a distant anode electrode might be utilized, placed at a distance from the grid to act as a return electrode. It may be advantageous to utilize multiple adjacent electrodes with the same polarity to create additive effects that produce distinct spatial current density distributions surrounding a particular region of the grid. In scheme 1, the utilization of three cathodes simultaneously may produce a generalized, relatively large current density distribution as the three cathodes act together to produce a distinct current density. FIG. 5 scheme 1 illustrates a scheme that might be considered for use early on in scan mode as it produces a generalized current density in quadrant 1 of the grid. FIG. 5 scheme 2 illustrates a similar stimulation scheme however the three electrodes designated as cathodes are in the right lower corner of the grid. In this scheme, electrodes K10, J11 and K11 are all designated as cathodes. This scheme also utilizes a distant anode electrode that is placed at a distance from the grid to act as a return electrode. This is another example of a scheme similar to scheme 1 that might produce a generalized current density in a particular quadrant that might be useful early on in scan mode for gross detection of evoked responses. FIG. 5 scheme 3 illustrates another example of a scheme that might be used early on in scan mode which produces a relatively large current density on the upper left quadrant of the grid to search for evoked potential responses. In this scheme, electrodes A1, B1 and C1 are designated as cathodes and A11, B11 and C11 are designated as anodes. It is suspected that this arrangement of active electrodes will produce a relatively diffuse current density in proximity to the left side of the grid with the highest current density in the left upper quadrant (area containing rows 1-6 and columns A-F). FIG. 5 illustrates how scan mode could perform a general scan of the left upper quadrant by utilizing scheme 3 followed by the reversing the polarity of scheme 3 as seen in scheme 4, with A11, B11 and C11 as cathodes and A1, B1 and C1 as anodes so that the highest current density would be delivered to the left lower quadrant (area containing rows 6-11 and columns A-F). The examples provided in FIG. 5 are for the purpose of illustrating how different combinations of active electrodes can be strategically assigned for a more generalized scanning of the quadrants early on in scan mode. Once responses are detected and localized to a generalized area, the software will employ algorithms which designed to guide subsequent stimulations with more specific stimulation schemes that will systematically hone in on the schemes which yield optimal evoked responses at the lowest stimulation intensity. The most effective way to design the specific programming of the scan algorithm are yet to be determined. This might be best determined from mathematical modeling and/or experiments and experience with a working system. Different applications might benefit from specifically designed scan algorithms. In some instances, it may be possible that the system determines that there are multiple different stimulation schemes that produce optimal evoked potential responses, with no appreciable difference when stimulating with any of those select schemes. In such instances, the system might be programmed to alert the operator that there are multiple stimulation schemes which yield optimal evoked potential responses.

Figure 6:
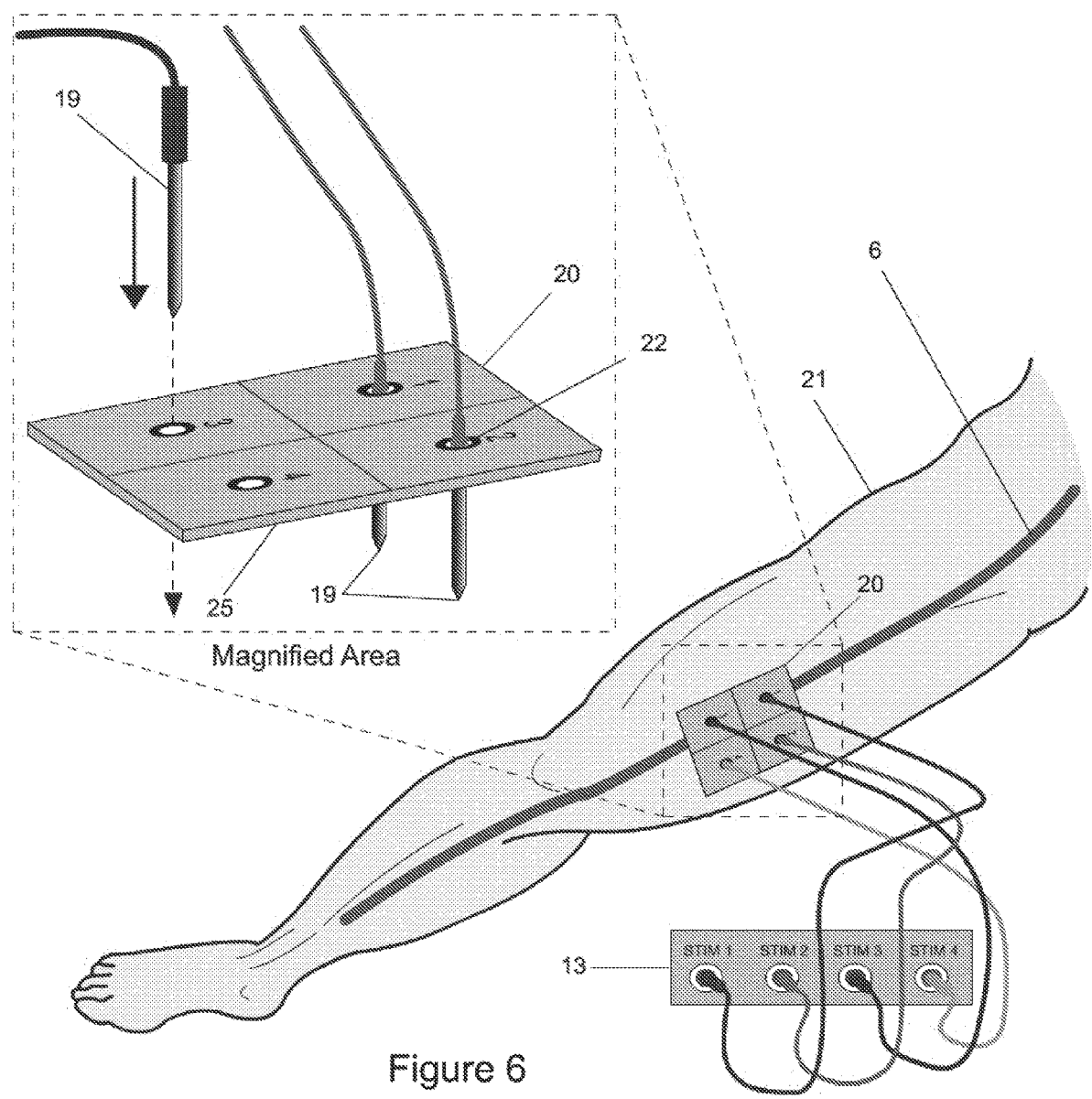
FIG. 6 illustrates an example an embodiment with an alternative version the grid system that allows for the ability to manually insert stimulating needle electrodes into the patient for a more precise electrode placement. The manual grid guide (20) comprises or consists essentially of a flexible substrate with an adhesive underside (25) that is placed on the patient's right leg (21) in an area thought to overlie the nerve of interest (6). In this particular example, the manual grid guide has 4 equidistantly spaced perforated holes (22) that are used to guide the placement of 4 subdermal needle electrodes (19). The needle electrodes are connected to the electrical power source (13) whose output is controlled by the software/computer system (14). Once the electrodes are manually placed into the grid configuration, the system can run multiple sequential different stimulation schemes to scan the grid searching for evoked potential responses and the optimal stimulation configuration and parameters.

FIG. 6 illustrates a different embodiment for the same application utilized in the main example for stimulating the saphenous nerve. FIG. 6 illustrates a cost-effective and simple option that allows for the manual placement of deep stimulating needle electrodes (19). In choosing the best trajectory for needle insertion to localize the saphenous nerve (6) in the patient's right leg (21), it may be advantageous for a clinician to maintain better fine dexterous control of the needles. In this particular embodiment, a manual grid guide constructed of a flexible, non-conductive substrate (20) with an adhesive bottom (25) is attached the patient's right leg (21) in an anatomical spot on the skin suspected to be overlying the location of the saphenous nerve. This embodiment illustrates the idea of utilizing a manual grid guide (20) to guide the placement of the stimulating electrode however a clinician has more control over the trajectory of the needle (19) insertion in contrast to the fixed position of stimulating needles (17) in the embodiment described in FIG. 2. The manual grid guide (20) in this embodiment, has four perforated, equidistantly spaced slots (22) through which each of the four stimulating needle electrodes (19) can be manually inserted. This embodiment offers more precise manual control of the trajectory of the needle placement which may be best inserted manually by a trained neurophysiologist or health care professional with an advanced understanding of the underlying anatomy and other technical considerations. It also may be useful to choose an effective trajectory for needle insertion with consideration of the contour of the patient's leg. After the needles are placed in the grid configuration, each of the stimulating electrodes are then connected to its' corresponding connection in the stimulating unit (13) so that the system can recognize the position of each electrode and employ a stimulation protocol to sequentially determine the optimal stimulation configuration and parameters using the scan mode methods described herein.

Figure 7:
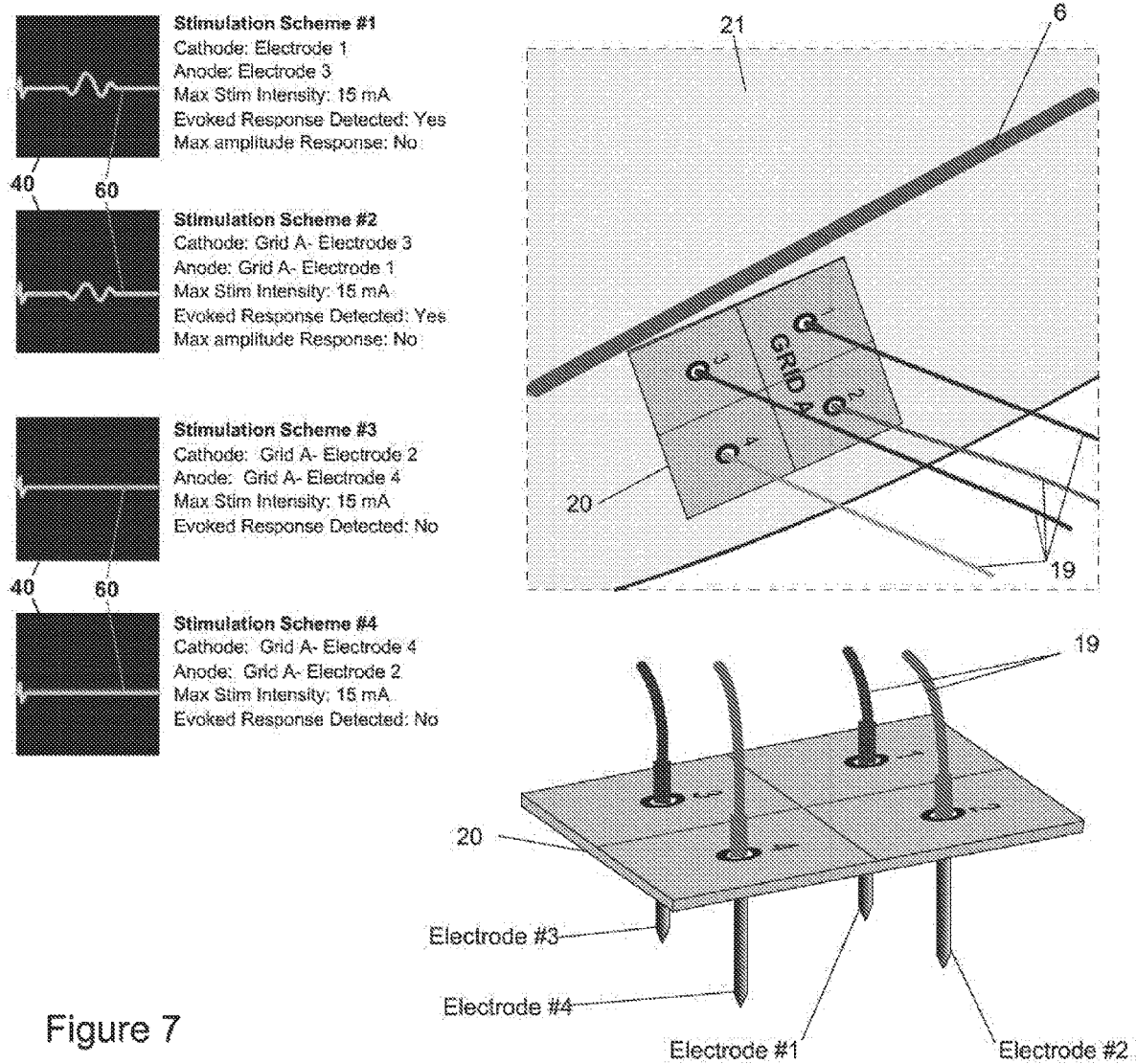
FIG. 7 illustrates a situation where the first manual grid guide A (20) is not placed in an optimal position over the underlying nerve of interest (6). In this example, information acquired and analyzed from scanning multiple different stimulation schemes using the first grid guide A (20) will alert the operator that placement of a second manual grid guide B (23) in a particular direction adjacent to the first manual grid guide may provide higher quality evoked potential responses. This is a hypothetical example of a situation where the system can determine that the placement of the first manual grid guide (20) may be sub-optimal and how the system can suggest placement of an additional grid guide in a specific direction that may improve the quality of the evoked potential responses.

FIG. 7 illustrates another possible embodiment related to FIG. 6 which illustrates a situation where the system is designed to detect that the first manual grid guide is not positioned optimally over the nerve of interest (6). This an example of how the system can detect a situation where the first grid guide (20) (labeled as grid guide A) might be placed in a sub-optimal position that is not directly over the nerve of interest and the system can guide the operator, advising them to place an additional adjacent manual grid guide in a particular direction relative to the position of the first grid guide (20). FIG. 7 illustrates a simplified example of how the system might be programmed to analyze the information gained from scanning different stimulation schemes and detect a situation where the first manual grid guide A (20) is placed in a sub-optimal position. In this particular example, the system might advise the operator of a specific direction for placement of an additional grid guide relative to grid guide A (20) based on the information gained from scanning multiple stimulation schemes using grid guide A (20) as shown. In FIG. 7, stimulation scheme 1, electrode #1 is designated as a cathode and electrode #3 is designated as an anode. In this example, this stimulation scheme appears to be effective to elicit an evoked response (60) as shown on the display monitor (40). In this example, with stimulation using scheme 1, the system detects an incrementally increasing amplitude response with incrementally increasing stimulation intensity until the system reaches the maximum stimulation intensity (that is arbitrarily set to 15 mA in this example). In FIG. 7 stimulation scheme 2, the electrodes from scheme 1 are reversed in polarity as electrode #3 is now designated as the cathode and electrode #1 is now designated as the anode. Stimulation using scheme 2 also appears to elicit an evoked response (60) at the set maximum stimulation intensity of 15 mA, although it appears to be slightly lower in amplitude than with stimulation using scheme 1. In contrast to schemes 1 and 2, schemes 3 and 4 utilize electrode #2 and electrode #4 as anode and cathodes and neither scheme results in an observable evoked potential response on the display (40) at the system maximum stimulation intensity of 15 mA. In this example, electrodes #2 and #4 are located even further posterior to the nerve compared to electrodes #1 and #3, and stimulation schemes that utilize electrodes #2 and #4 are expected to be less effective in activating the nerve and thus less likely to elicit a recordable evoked response. The information obtained from these four examples of stimulation schemes in FIG. 7 suggests that the nerve may located in closer proximity to electrodes #1 and #3 than electrodes #2 and #4 as is the case in this example. Although stimulation with schemes 1 and 2 elicit evoked potential responses, the system detects that the evoked potential responses have not reached their maximum amplitude at the system's maximum stimulation intensity of 15 mA. The system recognizes that the responses have not reached maximum amplitude as the analyzed evoked potential response amplitudes continue to incrementally increase as the system incrementally increases the stimulation intensity to the maximum stimulation intensity of 15 mA. In this hypothetical example, the system does not detect a maximum amplitude response. This information suggests that the nerve may not be fully activated with stimulation provided at the systems' designated maximum stimulation intensity of 15 mA. This information also suggests that it may be possible to improve the quality of the evoked potential responses by specifically placing a second grid guide in a more anterior position relative to the first grid guide as is illustrated in FIG. 8.

Figure 8:
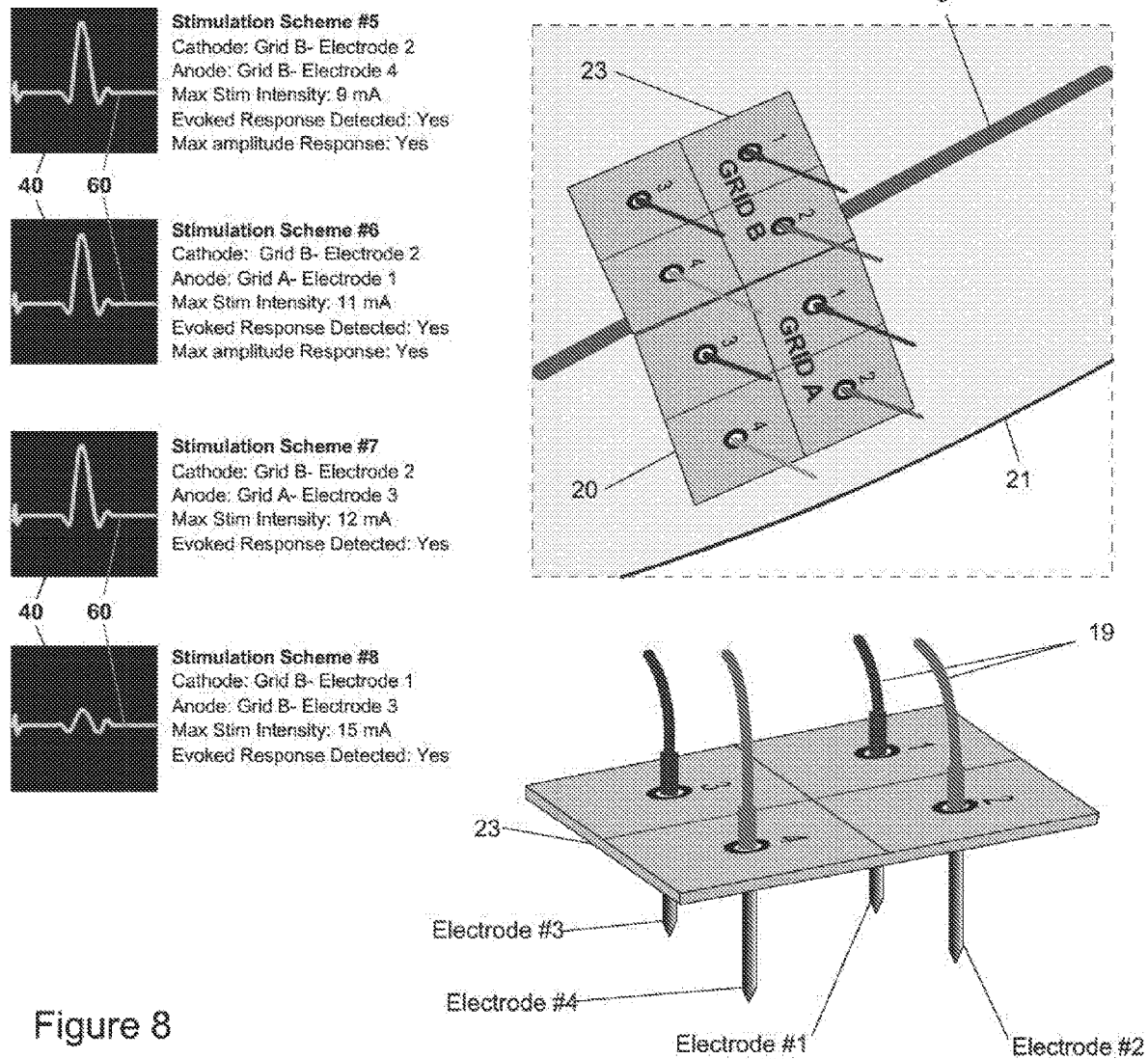
FIG. 8 illustrates a continuation of example provided in FIG. 7 with a second manual grid guide (23) placed adjacent to the first grid guide (20) in a more anterior direction as would be suggested from the information gained from a scan of evoked potential recordings obtained with various stimulations with the first grid guide as shown in FIG. 7. The second manual grid guide (23) lies in a position directly over the nerve of interest (6) and stimulations involving electrodes #2 and #4 (schemes 5, 6 and 7) yield even higher amplitude responses than those obtained from stimulation using the first grid guide in FIG. 7.

FIG. 8 illustrates a continuation of the situation described in FIG. 7 where the first grid guide A (20) is placed in a sub-optimal position that with electrodes that lie posterior to the nerve. In this hypothetical example in FIG. 7, information gained from multiple stimulation schemes utilizing the first grid guide (20) produces an alert to the operator that placement of an additional grid guide B (23), specifically a more anterior position, may improve the quality of the evoked potential responses. The system is designed to detect this situation and advise the operator to place a second grid guide B (23) in a position anterior and adjacent to grid guide A (20). Once in position, multiple sequential stimulation schemes are again applied utilizing grid guide B (23) as illustrated in the examples of 4 different schemes in FIG. 8. In FIG. 8, stimulation scheme 5 uses grid guide B (23) electrode #2 designated as a cathode and grid guide B (23) electrode #4 as an anode. In this hypothetical example, stimulation with scheme 5 only uses 9 mA of current for the system to detect that a maximum amplitude evoked potential response is obtained. Using stimulation scheme 5, any increase in the stimulation intensity above 9 mA does not further increase the amplitude of the evoked response. Thus, it is inferred that all of the axons that constitute the nerve trunk have been activated at 9 mA and a further increase in stimulation intensity will not improve the quality of evoked responses. In FIG. 8, stimulation scheme 6 utilizes grid guide B (23) electrode #2 designated as the cathode with grid guide B (23) electrode #1 as the anode. Stimulation with scheme 6 reveals a maximum amplitude response obtained with 11 mA of stimulation, which is slightly greater than the maximum amplitude response observed with scheme 5 which only uses 9 mA of stimulation intensity to achieve a maximum amplitude evoked response. In FIG. 8, scheme 7 illustrates how the system might use stimulation schemes that utilize active electrodes from both grid guide A (20) and grid guide B (23) which might be useful in finding the optimal combination of electrodes. In FIG. 8 scheme 7, grid guide B (23) electrode #2 is designated as the cathode and electrode #3 from grid guide A (20) is designated as the anode. With stimulation scheme 7, a maximum amplitude response is obtained at 12 mA. FIG. 8 scheme 8 illustrates a scheme that utilizes grid guide B (23) electrodes #1 as a cathode and #3 as an anode. These electrodes are located further anterior to the nerve than grid guide B (23) electrodes #2 and #4 and thus the evoked potential responses are lower in amplitude and a maximum amplitude response is not obtained at the system maximum stimulation intensity of 15 mA. In the example shown in FIG. 8, the most favorable combination of electrodes is observed in scheme 5 as the maximum amplitude of the evoked response is obtained utilizing the least amount of stimulation intensity (9 mA) compared to the other schemes shown. The examples of stimulation schemes illustrated in FIGS. 7 and 8 are simplified, bipolar stimulation schemes that are included here only for the purpose of illustrating the basic concepts of how these materials and methods can analyze evoked responses and determine the optimal electrode configuration and stimulation parameters for the acquisition of optimal evoked potential responses and/or provide directional information for the placement of additional manual grid guides which might result in higher quality evoked potentials which use lower stimulation intensities. Actual systems will likely utilize more complex stimulation schemes involving multipolar stimulation to rapidly "scan" the grid electrode using multiple variable sequential stimulation schemes in order to determine the optimal stimulation configuration and stimulation parameters that results in optimal evoked potential recordings and/or give directional information of how additional grids might be placed to obtain optimal results.

FIGS. 1 through 8 illustrate examples of embodiments designed for the purpose of intraoperative neuromonitoring. For intraoperative monitoring purposes, the completion of the scan mode should result in optimized "baseline" evoked potential recordings which are commonly documented at the beginning of a surgical procedure and used as a comparison for subsequent evoked potentials. Following acquisition of optimized "baseline" recordings from the completion of Scan Mode, the operator can continue on to Monitoring Mode where the optimized stimulation scheme and parameters can be used to continuously run evoked responses throughout a surgical procedure, comparing subsequent responses to the baseline recordings to detect any degradation of the responses during the surgical procedure.

Figure 9A:
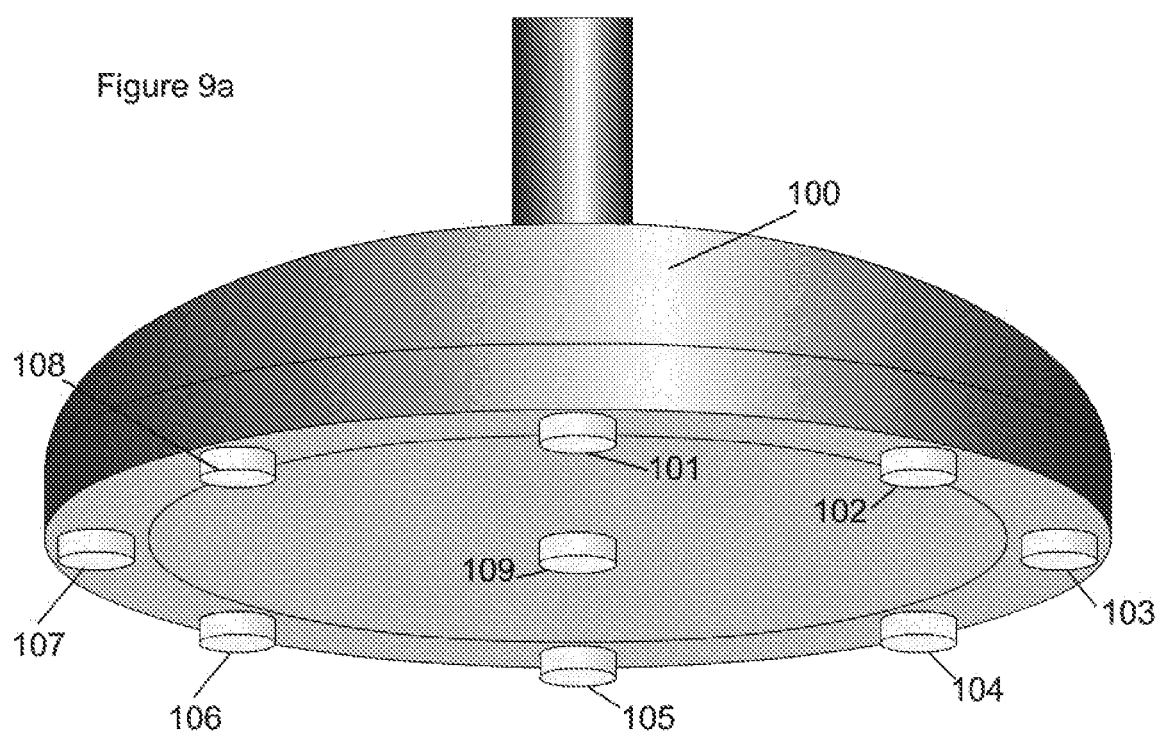
FIG. 9a illustrates a variant of the square grid electrodie configuration illustrating a circular arrangement of electrodes which can be utilized to obtain optimal evoked potential recordings by varying the stimulation configurations and parameters in a similar fashion as described for the square, grid shaped electrode configurations. In this embodiment, an example of a simple circular grid electrode (100) is illustrated, equipped with a plurality of electrodes (101, 102, 103, 104, 105, 106, 107, 108 and a central electrode 109).
Figure 9B:
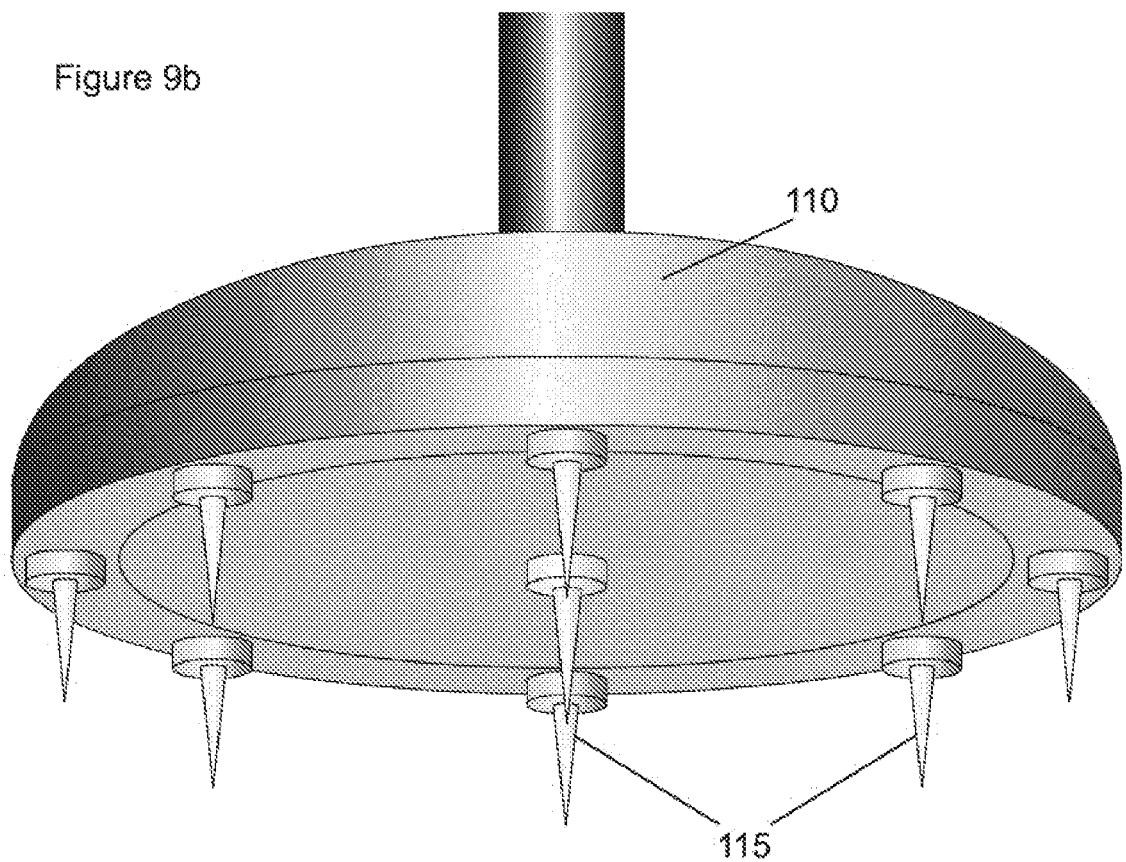
FIG. 9b illustrates a variant of electrode 100 as a similar circular grid electrode (115) but with needle electrodes (115) that could project through the skin which may be helpful to reduce the electrical impedance significantly and/or ensure the stimulation is delivered closer to the target nerve of interest.

FIGS. 9, 10 and 11 illustrate an additional embodiment of the grid electrode system as might be utilized with a circular electrode arrangement instead of a square arrangement. FIG. 9a illustrates a variant of the square grid electrode configuration illustrating a circular arrangement of electrodes which can be utilized to obtain optimal evoked potential recordings by varying the stimulation configurations and parameters in a similar fashion as described for the square, grid shaped electrode configurations. In this embodiment, a circular grid electrode (100) is equipped with a plurality of electrodes (101, 102, 103, 104, 105, 106, 107, 108 and a central electrode 109). As with prior examples of grid arrays, all electrodes are independently connected to the power source and can be assigned a specific polarity or rendered inactive. Similar to the square or rectangular grid arrays, software can scan the circular grid with a variety of stimulation schemes that will be aimed at obtaining the highest quality evoked potential responses while utilizing the least amount of stimulation intensity. FIG. 9b illustrates a variant of electrode 100 as a similar circular grid electrode (115) but with needle electrodes (115) that could project through the skin which may be helpful to reduce the electrical impedance significantly and/or ensure the stimulation is delivered closer to the target nerve of interest.

FIG. 10 illustrates the hypothetical current densities that might be generated surrounding the circular electrode (100) with an example of a simple clockwise sequence wherein electrodes are activated in a bipolar configuration in a 360-degree sweep with each scheme having the cathode and anode positioned 180 degrees directly across from one another. In this example a peripheral nerve (6) that is to be studied is located at a position near the circular electrode. In this simple example of a basic scan routine that could be employed, the first scheme in this sequence utilizes a bipolar configuration with electrode (101) as the cathode and electrode 105 as the anode with the resultant hypothetical current densities produced by this stimulation configuration which does not produce a current density that is sufficient to activate the nerve (6) as illustrated by a lack of an EMG response on the differential amplifier display (40). In the 2nd stimulation scheme in this example, the cathode is moved over 1 position clockwise to electrode 102 and the anode is also moved clockwise to electrode 106 with the resultant hypothetical current density illustrated which is also does not produce a sufficient current density to activate the nerve (6). In the 3rd stimulation scheme in this example, the cathode is moved one position clockwise to electrode 103 and the anode is also moved clockwise to electrode 107 with the resultant hypothetical current density illustrated which is also does not produce a sufficient current density to activate the nerve of interest. In the fourth stimulation in this example, the cathode is again moved one position over clockwise to electrode 104 and the anode is also moved clockwise to electrode 108 with the resultant hypothetical current density illustrated. The fourth stimulation configuration does create a current density that is sufficient to activate the some of the axons of the nerve and the EMG displays the resultant motor evoked potential response (120) that is recorded from differential amplification of muscle recordings from muscles innervated by the nerve of interest. Stimulations schemes 5-8 continue this pattern of sequential bipolar stimulation in a clockwise fashion, however none of these stimulation configurations result in a current density sufficient to activate the nerve with the exception of stimulation scheme number 4.

FIG. 11 illustrates the circular electrode (100) with a simple clockwise scan sequence of multi-polar stimulation utilizing a configuration using a central cathode surrounded by 2 anodes along with the hypothetical current densities that would be produced with each of 8 sequential stimulation schemes where in each successive stimulation, the cathode is switched to one position in the clockwise direction and is continually flanked by 2 anodes that equally share the anodic activation. Multipolar stimulations such as these may be found to be useful as they may be able to better confine the current distribution to a more focal area compared to broader bipolar configurations as shown in FIG. 10.

Figure 12:
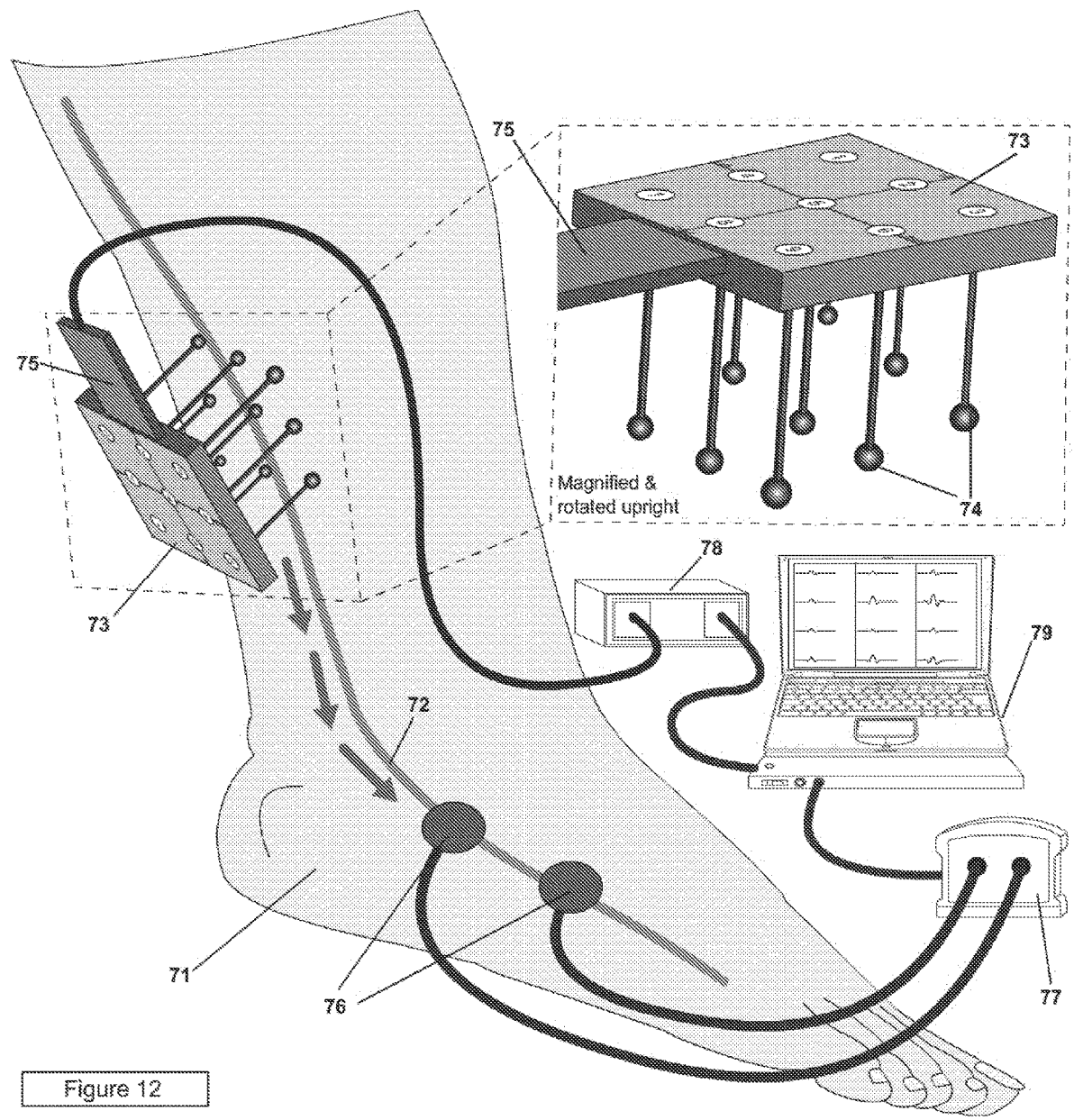
FIG. 12 illustrates an embodiment of these materials and methods as they might be applied to common nerve conduction studies. In this example, a common sural sensory nerve conduction study is illustrated using a specially designed 3×3 surface stimulating grid electrode (73) with three rows and columns of equidistantly spaced surface stimulating electrodes (74) that is powered by an electrical power source (78) which is controlled by software integrated with a differential amplification system (79) that controls the stimulation schemes and parameters based on information obtained from differential recordings from surface electrodes (76) which are connected to the system through a pre-amplifier (77). The grid electrode (73) is placed at a site on the patient's right lower leg (71) where the sural sensory nerve is suspected to be located, about 10 cm proximal to the surface recording electrodes (76) which are placed at a distal location above where the sural nerve is suspected to lie above. The surface electrodes (76) are placed over the sural sensory nerve to detect any evoked potentials (sensory nerve action potentials (SNAPs).

FIG. 12 illustrates an embodiment of these materials and methods as they might be applied to optimize common nerve conduction studies which have traditionally used a stimulating unit comprising only a single anode and a single cathode. This particular embodiment illustrates a handheld, 3×3 surface stimulating electrode grid (73) with three rows and columns of equidistantly spaced surface stimulating electrodes (74). Variations in the shape, size and spacing of the electrodes (74) on the grid (73) are expected to be utilized for different applications and patient sizes. This particular example is utilized only for the purposes of illustrating the basic principles involved, and other embodiments of these materials and methods are expected to be utilized. For example, instead of a rigid grid (73), a disposable, flexible grid with low profile surface electrodes with and adhesive surface can be utilized using the same stimulation search protocols described herein (not shown). In FIG. 12, an example of a rigid grid electrode stimulation system (73) is powered by an electrical power source (78) that delivers current to the tip of each electrode on the grid independently. In this particular example of how these techniques can be applied to common nerve conduction studies, the grid is utilized for the purpose of obtaining an optimal sural sensory nerve response to ensure adequate stimulation of the nerve and obtain an accurate diagnostic assessment of sural nerve function. Usually, a simple fixed bipolar electrode (a single anode and a single cathode) is used to stimulate the sural sensory nerve in a common antidromic sural sensory nerve conduction study. These materials and methods utilize a grid electrode system to systematically scan a relatively larger spatial area and ensure that the sural sensory nerve is optimally stimulated. In this embodiment, an electrical power source (78) is controlled by software integrated with a differential amplification system and display (79) that controls the stimulation schemes and parameters based on a mathematical analysis of information obtained from differential recordings from surface electrodes (76) which are connected to the system through a pre-amplifier (77). In this example of a common sural sensory nerve conduction study, the grid electrode (73) is placed at a site on the patient's right lower leg (71) where the sural sensory nerve is suspected to be located, about 10 cm proximal to the surface recording electrodes (76) as is commonly performed in standard nerve conduction studies. If the sural sensory nerve is sufficiently activated by electrical stimulation, an action potential will propagate antidromically (direction of arrows) towards the recording surface electrodes (76) which are placed over a position on the skin where the sural sensory nerve is suspected to be located. The recording electrodes (76) are connected to a differential amplification system (77). The system scans through different stimulation configurations to detect any evoked potentials (in this example: sensory nerve action potentials) that are elicited from various stimulation schemes of the grid (73). The system may have options where the stimulation schemes can be manually configured and controlled by the operator. Automated stimulation protocols may be utilized, however automated systems will likely have to be specifically designed as they may be more constrained in situations where these materials and methods are applied to nerve conduction studies that are performed on an awake patient (as opposed to the intraoperative neuromonitoring examples provided herein). Despite these constraints, the general process of searching for the optimal stimulation scheme will utilize similar algorithms as described in earlier sections. The automated system may apply incrementally increasing stimulation intensities to various permutations of stimulation schemes while analyzing the evoked potential recordings to hone in on the optimal combination of stimulating electrodes on the grid (73) and the optimal stimulation parameters that yield the most optimal (usually associated with highest amplitude) evoked potential responses that are obtained with utilizing the lowest amount of stimulation intensity. As described herein, the system is designed to detect when the nerve is maximally activated at a point where an increase in stimulation intensity does not increase the amplitude of the evoked response. A given stimulation scheme might be utilized with incremental increases in stimulation intensity until a maximum amplitude response is detected (or until a predetermined maximum stimulation intensity is reached). Once the system detects that the evoked response amplitude no longer increases in amplitude significantly with increasing stimulation intensity, the system recognizes that the present nerve axons are likely activated and no additional stimulation intensity will be used or useful. This type of automated system should eliminate the chance that the operator will overstimulate the patient with the hopes of diminishing some of the discomfort associated with the nerve conduction examination. Obtaining optimal evoked responses is a main goal of any nerve conduction study and these materials and methods could significantly reduce user associated technical errors and increase the interpreting physician's assurance that the diagnostic test results are accurate and useful for providing a clinical assessment of peripheral nerve function. These materials and methods may also help to significantly increase the physician's confidence that abnormal nerve conduction test results are likely due to true pathology and less likely a result of operator errors during the nerve conduction test itself, with the possibility of sub-optimal stimulation due to poor positioning of the stimulating electrodes and/or sub-optimal stimulating parameters which can undermine the accuracy of the diagnostic findings.

The foregoing description and examples has been set forth merely to illustrate the disclosure and are not intended as being limiting. Each of the disclosed aspects and embodiments of the present disclosure may be considered individually or in combination with other aspects, embodiments, and variations of the disclosure. In addition, unless otherwise specified, none of the steps of the methods of the present disclosure are confined to any particular order of performance. Modifications of the disclosed embodiments incorporating the spirit and substance of the disclosure may occur to persons skilled in the art and such modifications are within the scope of the present disclosure. Furthermore, all references cited herein are incorporated by reference in their entirety.

While the methods and devices described herein may be susceptible to various modifications and alternative forms, specific examples thereof have been shown in the drawings and are herein described in detail. It should be understood, however, that the invention is not to be limited to the particular forms or methods disclosed, but, to the contrary, the invention is to cover all modifications, equivalents, and alternatives falling within the spirit and scope of the various embodiments described and the appended claims. Further, the disclosure herein of any particular feature, aspect, method, property, characteristic, quality, attribute, element, or the like in connection with an embodiment can be used in all other embodiments set forth herein. Any methods disclosed herein need not be performed in the order recited. Depending on the embodiment, one or more acts, events, or functions of any of the algorithms, methods, or processes described herein can be performed in a different sequence, can be added, merged, or left out altogether (e.g., not all described acts or events are necessary for the practice of the algorithm). In some embodiments, acts or events can be performed concurrently, e.g., through multi-threaded processing, interrupt processing, or multiple processors or processor cores or on other parallel architectures, rather than sequentially. Further, no element, feature, block, or step, or group of elements, features, blocks, or steps, are necessary or indispensable to each embodiment. Additionally, all possible combinations, subcombinations, and rearrangements of systems, methods, features, elements, modules, blocks, and so forth are within the scope of this disclosure. The use of sequential, or time-ordered language, such as "then," "next," "after," "subsequently," and the like, unless specifically stated otherwise, or otherwise understood within the context as used, is generally intended to facilitate the flow of the text and is not intended to limit the sequence of operations performed. Thus, some embodiments may be performed using the sequence of operations described herein, while other embodiments may be performed following a different sequence of operations.

The various illustrative logical blocks, modules, processes, methods, and algorithms described in connection with the embodiments disclosed herein can be implemented as electronic hardware, computer software, or combinations of both. To clearly illustrate this interchangeability of hardware and software, various illustrative components, blocks, modules, operations, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can also be implemented as a combination of computing devices. e.g., a combination of a DSP and a microprocessor, a plurality of microprocessors, one or more microprocessors in conjunction with a DSP core, or any other such configuration.

The blocks, operations, or steps of a method, process, or algorithm described in connection with the embodiments disclosed herein can be embodied directly in hardware, in a software module executed by a processor, or in a combination of the two. A software module can reside in RAM memory, flash memory. ROM memory, EPROM memory, EEPROM memory, registers, hard disk, a removable disk, an optical disc (e.g., CD-ROM or DVD), or any other form of volatile or non-volatile computer-readable storage medium known in the art. A storage medium can be coupled to the processor such that the processor can read information from, and write information to, the storage medium. In the alternative, the storage medium can be integral to the processor. The processor and the storage medium can reside in an ASIC. The ASIC can reside in a user terminal. In the alternative, the processor and the storage medium can reside as discrete components in a user terminal.

Conditional language used herein, such as, among others, "can," "might," "may," "e.g.," and the like, unless specifically stated otherwise, or otherwise understood within the context as used, is generally intended to convey that some embodiments include, while other embodiments do not include, certain features, elements, and/or states. Thus, such conditional language is not generally intended to imply that features, elements, blocks, and/or states are in any way required for one or more embodiments or that one or more embodiments necessarily include logic for deciding, with or without author input or prompting, whether these features, elements and/or states are included or are to be performed in any particular embodiment.

The methods disclosed herein may include certain actions taken by a practitioner; however, the methods can also include any third-party instruction of those actions, either expressly or by implication. For example, actions such as "positioning a grid array" include "instructing positioning of a grid array."

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±5%, ±10%, ±15%, etc.). For example, "about 15 mA" includes "15 mA." Phrases preceded by a term such as "substantially" include the recited phrase and should be interpreted based on the circumstances (e.g., as much as reasonably possible under the circumstances). For example, "substantially perpendicular" includes "perpendicular." Unless stated otherwise, all measurements are at standard conditions including temperature and pressure. The phrase "at least one of" is intended to require at least one item from the subsequent listing, not one type of each item from each item in the subsequent listing. For example, "at least one of A, B, and C" can include A, B, C, A and B, A and C, B and C, or A. B, and C.

The entire disclosures of each of the references noted herein are hereby made part of this specification as if set forth fully herein and incorporated by reference for all purposes, for all that it contains, including U.S. Patent Pub. No. 2013/0035741; U.S. Patent Pub. No. 2011/0269172; U.S. Pat. No. 8,644,903; U.S. Patent Pub. No. 2005/0182456; U.S. Pat. Nos. 8,224,453; 8,914,121; U.S. Patent Pub. No. 2011/0230785; U.S. Patent Pub. No. 2014/0114168; AHMADIAN et al., Analysis of lumbar plexopathies and nerve injury after lateral retroperitoneal transpsoas approach: Diagnostic standardization, J. Neurosurg. Spine, 2013, 18(3):289-97; SILVERSTEIN et al., Saphenous nerve somatosensory evoked potentials: A novel technique to monitor the femoral nerve during transpsoas lateral lumbar interbody fusion, Spine (Phila Pa. 1976), 2014, 39(15): 1254-60; ROBINSON et al., The efficacy of femoral nerve intraoperative somatosensory evoked potentials during surgical treatment of thoracolumbar fractures, Spine (Phila Pa. 1976). Oct. 1, 1993, 18(13):1793-7, PMID: 8235863; BLOCK et al., Motor evoked potentials for femoral nerve protection in transpsoas lateral access surgery of the spine, Nueordiagnostic Journal. March 2015, 55(1):36-45; and CHAUDHARY et al., Trans-cranial motor evoked potential detection of femoral nerve injury in trans-psoas lateral lumbar interbody fusion, Journal of Clinical Monitoring and Computing, Jun. 17, 2015, PMID: 26076805.

What is claimed is:

1. A system configured to enhance diagnostic evoked potential recordings of a nerve or nerve pathway, the system comprising:
   a plurality of stimulating electrodes arranged in a grid array configured to be placed on, over, or through skin over an area of a nerve or nerve pathway;
   a stimulator configured to control the grid array, wherein:
      each of the plurality of stimulating electrodes is independently assignable to be active or inactive,
      each of the plurality of stimulating electrodes is independently assignable to be active as an anode or a cathode, and
      the stimulator is configured to independently assign stimulation parameters to each of the plurality of stimulating electrodes;
   a plurality of recording electrodes configured to record at least one of
      Somato-Sensory Evoked Potentials (SSEPs) or
      Transcranial Electrical Motor Evoked Potentials (TCeMEP); and
   a processor configured to automatically execute a general search mode and a focused search mode after the general search mode,
   the general search mode comprising instructing the stimulator to systematically test a plurality of stimulation schemes until an evoked potential response is detected by the plurality of recording electrodes having a maximum response amplitude,
   each of the plurality of stimulation schemes of the general search mode including activating and assigning positions and polarity of one or more of the plurality of stimulating electrodes,
   the general search mode further comprising instructing the stimulator to ramp stimulation intensity of a stimulation during testing each of the plurality of stimulation schemes until either:
      a maximum stimulation intensity value is reached, or
      a maximum response amplitude is detected,
   wherein the maximum response amplitude is an evoked potential response that does not increase in amplitude upon an increase in stimulation intensity,
   wherein a stimulation scheme of the plurality of stimulation schemes at which the maximum response amplitude is detected comprises a positive stimulation scheme,
   the focused search mode comprising utilizing information from the positive stimulation scheme to instruct the stimulator to systematically test the plurality of stimulation schemes until an evoked potential recording is detected by the plurality of recording electrodes having the maximum response amplitude and a minimum stimulation intensity,
   the focused search mode further comprising instructing the stimulator to ramp the stimulation intensity during testing each of the plurality of stimulation schemes until the maximum response amplitude is detected,
   the focused search mode further comprising:
      recording stimulation intensities during testing each of the plurality of stimulation schemes at which the maximum response amplitude is detected,
      comparing the stimulation intensities at which the maximum response amplitude was detected, and
      selecting the minimum stimulation intensity at which the maximum response amplitude was detected;
   wherein the processor is further configured to use the minimum stimulation intensity at which the maximum response amplitude was detected to continually stimulate the nerve or the nerve pathway.

2. A computer-implemented method for enhancing diagnostic evoked potential recordings of a nerve or nerve pathway, the method comprising:
   by one or more processors executing program instructions:
      communicating with a stimulator configured to control a grid array of a plurality of stimulating electrodes, wherein:
         the plurality of stimulating electrodes are arranged in the grid array and configured to be placed on, over, or through skin over an area of a nerve or nerve pathway,
         each of the plurality of stimulating electrodes is independently assignable to be active or inactive,
         each of the plurality of stimulating electrodes is independently assignable to be active as an anode or a cathode, and
         the stimulator is configured to independently assign stimulation parameters to each of the plurality of stimulating electrodes;
      automatically executing a general search mode and a focused search mode after the general search mode,
         the general search mode comprising instructing the stimulator to systematically test a plurality of stimulation schemes until an evoked potential response is detected by a plurality of recording electrodes having a maximum response amplitude,
         wherein the plurality of recording electrodes is configured to record at least one of
            Somato-Sensory Evoked Potentials (SSEPs) or
            Transcranial Electrical Motor Evoked Potentials (TCeMEP),
         each of the plurality of stimulation schemes of the general search mode including activating and assigning positions and polarity of the plurality of stimulating electrodes, the general search mode further comprising instructing the stimulator to ramp stimulation intensity of a stimulation during testing each of the plurality of stimulation schemes until either:
  a maximum stimulation intensity value is reached, or
  a maximum response amplitude is detected,
  wherein the maximum response amplitude is an evoked potential response that does not increase in amplitude upon an increase in stimulation intensity, and
  wherein a stimulation scheme of the plurality of stimulation schemes at which the maximum response amplitude is detected comprises a positive stimulation scheme,
the focused search mode comprising utilizing information from the positive stimulation scheme to instruct the stimulator to systematically test the plurality of stimulation schemes until an evoked potential recording is detected by the plurality of recording electrodes having the maximum response amplitude and a minimum stimulation intensity,
the focused search mode further comprising instructing the stimulator to ramp the stimulation intensity during testing each of the plurality of stimulation schemes until the maximum response amplitude is detected,
the focused search mode further comprising:
  recording stimulation intensities during testing each of the plurality of stimulation schemes at which the maximum response amplitude is detected,
  comparing the stimulation intensities at which the maximum response amplitude was detected, and
  selecting the minimum stimulation intensity at which the maximum response amplitude was detected; and
    using the minimum stimulation intensity at which the maximum response amplitude was detected to continually stimulate the nerve or the nerve pathway.

3. The method of claim 2, wherein the general search mode further comprises, after the evoked potential recording is detected, executing another stimulation scheme.

4. The method of claim 2, wherein the plurality of stimulating electrodes of the grid array are arranged in aligned rows and columns having four corners.

5. The method of claim 4, wherein at least one of the general search mode or the focused search mode comprises a first stimulation scheme of the plurality of stimulation schemes in which at least two corner positioned electrodes of the grid array are assigned to be active electrodes.

6. The method of claim 2, wherein the stimulating electrodes of the plurality of stimulating electrodes are at least one of: percutaneous or transcutaneous.

7. The method of claim 2, wherein the plurality of stimulating electrodes of the grid array are arranged in a circular pattern.

8. The method of claim 2, wherein at least one of the plurality of stimulating electrodes of the grid array comprises an atraumatic tip.

9. The method of claim 2, wherein the grid array is configured to be placed on at least one of: a limb or a head.

10. The method of claim 9, wherein the plurality of recording electrodes is configured to be placed on at least one of: a head, a limb, or a muscle.

11. The method of claim 2, wherein the grid array is configured to be placed on a first appendage and the plurality of recording electrodes is configured to be placed on a second appendage different than the first appendage.

12. The method of claim 2, wherein the grid array comprises a plurality of smaller grid arrays each configured to stimulate multiple points along a course of the nerve or nerve pathway.

13. The method of claim 2, further comprising:
  by the one or more processors executing program instructions:
    in response to receiving an input from a safety button capable of being pressed by an awake subject, immediately stopping all stimulation.

14. The method of claim 2, further comprising:
  by the one or more processors executing program instructions:
    in response to receiving an input from a user control, modifying at least one of the general search mode or the focused search mode by limiting a total number of the plurality of stimulation schemes used during the at least one of the general search mode or the focused search mode.

15. The method of claim 2, further comprising semi-automatically executing the general search mode and the focused search mode after the general search mode, wherein at least one of the general search mode or the focused search mode is interruptible by a user.

16. The method of claim 2, wherein the plurality of recording electrodes is configured to record Somato-Sensory Evoked Potentials (SSEPs), the SSEPs providing a user with a continuous functional assessment of the nerve or nerve pathway during a procedure in which the nerve or nerve pathway is known to be at risk of damage.

17. The method of claim 2, wherein the plurality of recording electrodes is configured to record Transcranial Electrical Motor Evoked Potentials (TCeMEP), the TCeMEPs providing a user with a functional assessment of the nerve or nerve pathway during a procedure in which the nerve or nerve pathway is known to be at risk of damage.

18. The method of claim 2, wherein the plurality of recording electrodes is configured to record Compound Muscle Action Potentials (CMAPs), the CMAPs providing a user with a functional assessment of peripheral motor nerve function.

19. The method of claim 2, wherein the plurality of recording electrodes is configured to record Sensory Nerve Action Potentials (SNAPs), the SNAPs providing a user with a functional assessment of peripheral sensory nerve function.

20. The method of claim 2, wherein the plurality of recording electrodes is configured to record Mixed Nerve Action Potentials (MNAPs), the MNAPs providing a user with a functional assessment of peripheral mixed nerve function.

* * * * *